Figure 1:
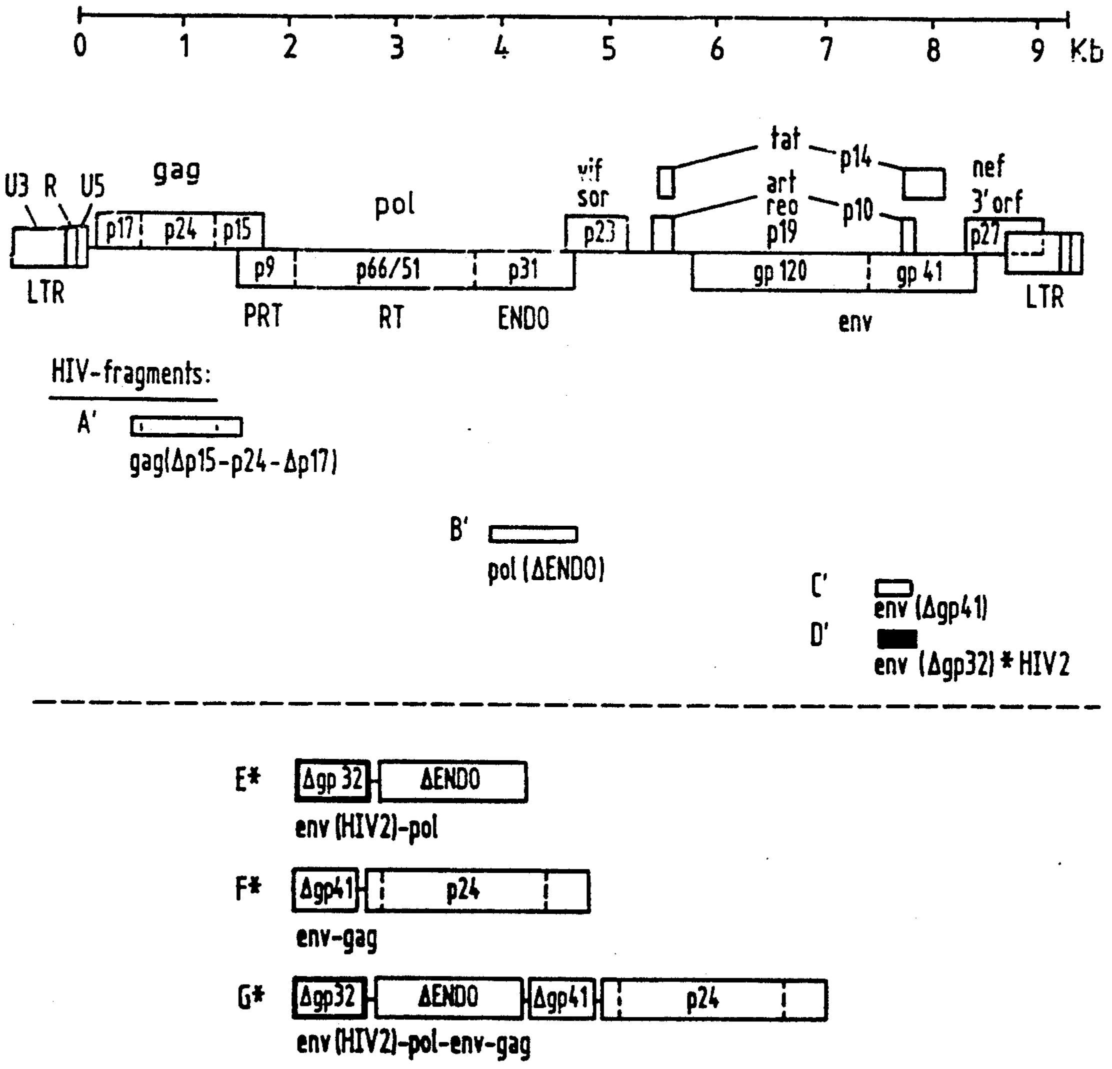

US005310876A

United States Patent [19]

Bayer et al.

[11] Patent Number: 5,310,876

[45] Date of Patent: May 10, 1994

[54] EXPRESSION OF HIV1 AND HIV2 POLYPEPTIDES AND THEIR USE

[75] Inventors: Hubert Bayer, Weilheim; Erhard Kopetzki, Penzberg, both of Fed. Rep. of Germany

[73] Assignee: Boehringer Mannheim GmbH, Mannheim-Waldhof

[21] Appl. No.: 648,796

[22] Filed: Jan. 25, 1991

[30] Foreign Application Priority Data

Jan. 30, 1990 [DE] Fed. Rep. of Germany ....... 4002636

[51] Int. Cl.[5] .......................... C07K 3/00; C12Q 1/70; C07H 15/12

[52] U.S. Cl. ........................................ 530/350; 435/5; 935/12; 536/23.72; 424/89

[58] Field of Search .............. 530/350; 435/5; 536/27; 935/12

[56] References Cited

FOREIGN PATENT DOCUMENTS

| | | | |
|---|---|---|---|
| 0331961 | 2/1989 | European Pat. Off. ...... | C12P 21/00 |
| 0416673AI | 8/1990 | European Pat. Off. ..... | C12N 15/62 |
| WO05440 | 1/1988 | PCT Int'l Appl. ............ | C07K 7/10 |

OTHER PUBLICATIONS

Guyader, et al., 1987, "Genome organization and transactivation of . . . " Nature 326: 662–669.

Shoeman, et al, 1987, "Comparison of recombinant human immunodeficiency . . . " Analytical Biochem. 161:370–379.

Cabradilla, et al., 1986, "Serodiagnosis of antibodies to the human AIDS . . . " Bioltechnology 4:128–133.

Structural Requirements for Bacterial Expression of Stable, Enzymatically Active Fusion Proteins Containing the Human Immunodeficiency Virus Reverse Transcriptase, DNA, vol. 7, No. 6, 1988, pp. 407–416, by Naoko Tanese et al.

European Search Report, Mar. 9, 1993, EP 91 10 1224.

*Primary Examiner*—Christine M. Nucker
*Assistant Examiner*—Lynette F. Smith
*Attorney, Agent, or Firm*—Felfe & Lynch

[57] ABSTRACT

A fusion protein with at least one antigenic and/or immunogenic determinant from the env, gag and/or pol region of HIV1 and/or HIV2 which contains the tetrapeptide sequence $NH_2$-Met-Tyr-Tyr-Leu as the N-terminal component as well as a process for its production and use.

4 Claims, 2 Drawing Sheets

Localisation of the HIV determinants on the HIV1 genome

Cloning strategy

EXPRESSION OF HIV1 AND HIV2 POLYPEPTIDES AND THEIR USE

DESCRIPTION

The invention concerns an improvement of the expression of polypeptides from the gag, env and pol region of HIV1 and HIV2 in microorganisms as host cells. In addition, it concerns a method and a reagent for the detection of anti-HIV antibodies in human body fluids.

An infection with HIV1 or HIV2 is usually detected by the presence of anti-HIV antibodies in human body fluids. HIV polypeptides are required for the detection of the anti-HIV antibodies. As a consequence, it is necessary to produce immunogenically active HIV polypeptides in adequate amounts in order to carry out a large number of AIDS tests. This production is usually carried out in bacteria by genetic engineering.

Thus, the expression of antigens from HIV1 and HIV2 in *E. coli* as "non-fusion proteins" (without a heterologous fusion component) is known from DE-OS 37 24 016. A disadvantage of this procedure is that in many cases these HIV polypeptides are only expressed to a very small extent. In addition, HIV polypeptides are often only sparingly soluble as a result of their hydrophobicity and are thus very difficult to purify.

In addition, it is known that HIV polypeptides can be produced as fusion proteins having HIV components and bacterial polypeptide components. By this means an improvement in the level of expression is achieved in many cases. EP-A-0 316 659 discloses the expression of fusion proteins which have determinants from HIV1 and HIV2, a carrier polypeptide component, which is derived in particular from the *E. coli* chloramphenicol acetyltransferase or the dihydrofolate reductase of the mouse, and an affinity polypeptide component, preferably a peptide with histidine residues. The use of such fusion proteins for the detection of anti-HIV antibodies is however limited since antibodies against the fusion partners used can occur in normal human sera which leads to false positive test results.

The object of the invention was therefore to achieve a high expression of HIV fusion polypeptides in microorganisms without these polypeptides having immunogenic determinants which could interfere with the HIV test by a reaction with normal human sera.

The invention therefore provides a fusion protein with at least one antigenic or/and immunogenic determinant from the env, gag or/and pol region of HIV1 or/and HIV2 which contains the tetrapeptide sequence $NH_2$-Met-Tyr-Tyr-Leu as the N-terminal component.

Surprisingly it was found that the amino acid sequence $NH_2$-Met-Tyr-Tyr-Leu of lactose permease (lacY) from *E. coli* as the N-terminal component improves the stability of HIV fusion proteins with at least one antigenic or/and immunogenic determinant of HIV1 or/and HIV2 and thus results in a significant improvement in the level of expression in *E. coli* as host cells. Thus, when using a suitable expression vector the level of expression of HIV1 and HIV2 fusion proteins is increased by a factor of ca. 10 by the N-terminal fusion of the tetrapeptide sequence $NH_2$-Met-Tyr-Tyr-Leu. No increased reactivity against such fusion proteins according to the present invention is found in normal human serum.

Furthermore, the fusion proteins according to the present invention can contain a cluster of several, preferably 4 to 30, charged hydrophilic amino acids as an additional component. In this way the solubility of hydrophobic HIV fusion proteins can be considerably improved and as a result the formation of insoluble protein aggregates can be substantially or completely prevented and as a consequence the handling of the fusion proteins with respect to isolation and use in the HIV test was considerably improved.

Particularly preferred are fusion proteins according to the present invention which contain a sequence of 4 to 30 basic amino acids (Lys and Arg) at the C-terminus. By this means the isoelectric point of a protein can be shifted to very basic values whereby the purification by ion-exchange chromatography is considerably facilitated The C-terminal poly(Arg, Lys) tag can, if desired, be subsequently removed by enzymatic means using carboxypeptidase B (Brewer and Sassenfeld, G. D. Searle, EPA 0 089 626 A2; Brewer and Sassenfeld, Gene 32 (1984) 321–327; Brewer and Sassenfeld, Trends in Biotechnology 3 (1985) 119–122).

Fusion proteins according to the present invention contain at least one immunogenic determinant from the env, gag or/and pol region of HIV1 or/and HIV2. DNA sequences which code for such determinants are obtainable from the proviral genome of HIV1 or HIV2 by conventional molecular biological procedures. Such DNA sequences can be coded in the reading frame in a suitable expression vector preceding a sequence coding for the tetrapeptide sequence $NH_2$-Met-Tyr-Tyr-Leu (MYYL) so that a recombinant gene is obtained which codes for a fusion protein according to the present invention. The DNA sequence regions A', B' and C' from the HIV1 genome are preferred.

The DNA sequence A' is a ca. 960 bp long Pvu/BglII fragment from the gag region of HIV1 and codes for 318 amino acids. A' is contained in the DNA sequence A shown in SEQ ID NO:9 which codes for a fusion protein with the amino acid sequence I (SEQ ID NO:1) consisting of the N-terminal tetrapeptide sequence MYYL, 3 amino acids of the vector, 317 amino acids from the gag region of HIV1 and a C-terminal vector sequence of 13 amino acids.

The DNA sequence B' is a ca. 710 bp long PvuII/BspMI fragment from the pol region of HIV1 which codes for 234 amino acids. B' is contained in the DNA sequence B shown in SEQ ID NO:10, which codes for a fusion protein with the amino acid sequence II (SEQ ID NO:2) consisting of the N-terminal tetrapeptide sequence MYYL, 3 amino acids of the vector, 234 amino acids from the pol region of HIV1 and a C-terminal vector sequence of 6 amino acids.

The DNA sequence C' is a ca. 310 bp long RsaI/HindIII fragment from the env region of HIV1 which codes for 101 amino acids. The DNA sequence C' is contained in the DNA sequence C shown in SEQ ID NO:11 which codes for a fusion polypeptide with the amino acid sequence III (SEQ ID NO:3) consisting of the N-terminal tetrapeptide sequence MYYL, 22 amino acids of the vector, 101 amino acids from the env region of HIV1 and a C-terminal vector sequence of 12 amino acids.

As a consequence of the construction further sequence regions from the vector are located between the DNA sequence coding for the peptide sequence MYYL and the HIV DNA, as well as on the 3' side of the HIV DNA fragment. These vector sequences should preferably not code for more than approximately 50 amino acids. It is important that these amino acid sequences cannot form any antigenic determinants which are recognized by human antibodies and thus interfere with the HIV test.

The DNA sequences coding for immunogenic HIV determinants can, however, also be produced from synthetic oligonucleotides as described below in more detail. The synthetically produced DNA sequence D' from the env region of HIV2 (cf. Example 2) codes for 115 amino acids. D' is contained in the DNA sequence shown in SEQ ID NO:12 which codes for a fusion polypeptide with the amino acid sequence IV (SEQ ID NO:4) consisting of the N-terminal tetrapeptide sequence MYYL, two amino acids of the vector, 115 amino acids from the env region of HIV2 and a C-terminal vector sequence of 9 amino acids.

Furthermore, the invention also concerns the production and use of "multifunctional HIV fusion proteins" which, apart from the N-terminal fusion sequences, also contain several antigenic determinants of the gag, pol and env regions of HIV1 and/or HIV2. These have the advantage that, instead of several different HIV polypeptides or proteins, only one multifunctional HIV fusion protein has to be fermented, purified and used in a HIV antibody detection test and as a consequence the costs can be considerably reduced. The multifunctional fusion proteins particularly preferably contain determinants of HIV1 and HIV2 so that antibodies against HIV1 and HIV2 can be detected simultaneously in one test. Multifunctional fusion proteins are also possibly of interest as immunogens, in particular for HIV vaccines.

The amino acid sequences of particularly preferred multifunctional fusion proteins and the DNA sequences which code for them are shown in the sequence protocols (SEQ ID NO:5 to 8 or SEQ ID NO:13 to 16). The amino acid sequence V represents a HIV fusion protein with determinants from the env (101 amino acids) and the gag region (317 amino acids) of HIV1. This amino acid sequence corresponds to the DNA sequence E which contains the DNA sequences C' and A'. The amino acid sequence VI and the DNA sequence F coding for it (with the DNA sequences D' and B') represent a HIV fusion protein with determinants from the env region (114 amino acids) of HIV2 and the pol region (234 amino acids) of HIV1. The amino acid sequence VII and the DNA sequence G coding for it (with the DNA sequences D', B', C' and A') represent a HIV fusion protein with determinants from the env region (114 amino acids) of HIV2 as well as the pol (234 amino acids), env (10 amino acids) and gag region (317 amino acids) of HIV1.

Furthermore, the invention provides recombinant DNA molecules which code for the fusion proteins according to the present invention. These DNA sequences are composed of the DNA sequence coding for the tetrapeptide sequence $NH_2$-Met-Tyr-Tyr-Leu, if desired, the vector sequences introduced by the construction, the DNA sequences coding for the HIV determinants and, if desired, the DNA sequence coding for a cluster of several charged amino acids. An example of this is the amino acid sequence VIII and the DNA sequence H which codes for it (with the DNA sequences D', B' and C' as well as a large part of the DNA sequence A') which represents a HIV fusion protein with determinants from the env region (114 amino acids) of HIV2, the pol (234 amino acids), env (101 amino acids) and gag region (287 amino acids) of HIV1, as well as a C-terminal poly(Lys, Arg) sequence (13 amino acids).

The DNA sequences coding for immunogenic HIV determinants can be obtained directly from the proviral DNA or by chemical gene synthesis as described previously. FIG. 1 shows the regions of HIV1 or the corresponding region of HIV2 from which the particularly preferred proviral DNA sequences according to the present invention are derived. In order to further improve the expression, synthetic DNA sequences which code for corresponding HIV polypeptides can be produced taking into account the codon usage of the employed host organism (e.g. *E. coli*) which is known to the expert. When designing synthetic genes care must also be taken that the formation of secondary structures is minimized, preferably suitable single restriction cleavage sites can also be inserted. The deoxyoligonucleotides used for the production of the synthetic DNA sequence D' and the cloning strategy are shown in detail in FIG. 2, the sequence protocols 17–26 and in Example 2.2.

Furthermore, the invention provides recombinant vectors with at least one copy of one or more recombinant DNA sequences according to the present invention. The vector can integrate itself in the genome of the host cell (e.g. vectors of the bacteriophage λ in *E. coli*) it is, however, preferably present extrachromosomally and particularly preferably in a high copy number. The recombinant vector is preferably suitable for gene expression in microorganisms, in particular *E. coli*, and has the necessary genetic elements for this (e.g. origin of replication, selection marker, promoter, terminator, etc.).

Vectors are particularly preferred in which the DNA sequence coding for a fusion protein according to the present invention is under the control of a promoter capable of being regulated (e.g. trp/lac fusion promoter for the gene expression in *E. coli*). In addition it is preferable that the recombinant vector contains one or more transcription terminators (e.g. the terminators $T_1$ and $T_2$ from the *E. coli* rrnB ribosomal RNA operon, Brosius et al., J. Mol. Biol. 148 (1981), 107–127) at the 3' end of the fusion gene. An example for a particularly suitable expression vector in *E. coli* is pKK233-2 (LKB-Pharmacia) having the trc promoter which is capable of being regulated and the terminators $T_1$ and $T_2$.

The invention also provides a microorganism which is transformed with a recombinant vector according to the present invention or with a recombinant DNA molecule according to the present invention. This microorganism is preferably an *E. coli* cell.

The strains which are suitable as *E. coli* strains are e.g. RM82lac+ (a methionine and lactose revertant of ED8654, Murray et al., Mol. Gen. Genet. 150 (1977), 53–61), HB101 (Maniatis et al., (1982), Molecular Cloning: A Laboratory Manual. Cold Spring Harbor Laboratory Press, Cold Spring Harbor, N.Y.) and K165 (Neidhardt and Van Bogelen, Biochem. Biophys. Res. Commun. 100 (1981) 884–900) and also further strains.

In a preferred embodiment of the present invention the transformed *E. coli* strain is cotransformed with a further compatible plasmid. When using a promoter which can be regulated by lactose (e.g. lac promoter, trp/lac fusion promoter) the compatible plasmid contains e.g. a lacI (Fabaugh, Nature 274 (1978) 765–769) or a $lacI^q$ repressor gene (Calos, Nature 274 (1978) 762–765) such as e.g. the plasmid pFDX500 which is a derivative of pACYC177 (Chang and Cohen, J. Bacteriol. 134 (1978) 1141–1156) or the F' episome from *E.*

*coli* JM109 (Yanisch-Perron et al., Gene 33 (1985) 103–109) which contain the lacI$^q$ repressor gene.

The additional presence of such repressor plasmids can improve the expression of HIV fusion proteins. However, a cotransformed repressor plasmid can also be used which contains in addition a gene for the t-RNA for Arg (anticodons: AGA, AGG) which is rare in *E. coli*, e.g. the dnaY-lacI$^q$ plasmid pUBS500 (EP-A 0368342). Surprisingly, it was found that the expression of HIV fusion proteins can be improved further by the presence of a dnaY-lacI$^q$ plasmid.

The invention provides in addition processes for the production of HIV fusion proteins in which suitable microorganisms, preferably *E. coli* cells, are transformed with a recombinant DNA molecule or vector according to the present invention on which a gene is located which codes for a HIV fusion protein according to the present invention and the fusion protein is isolated from the cells or from the medium according to conventional biochemical methods.

In this process the fusion proteins according to the present invention which contain an aid to separation, e.g. a cluster of charged amino acids, can be easily separated from the other cellular components by ion-exchange chromatography.

In a preferred process for the production of the HIV fusion proteins according to the present invention, the expression of the gene coding for the fusion protein is repressed during the growth phase e.g. by the presence of a repressor. Gene expression then first takes place on induction, e.g. by addition of an inducer.

Furthermore, a process is preferred in which a microorganism is used in which the gene coding for the recombinant fusion protein and a repressor gene are present at the same time (e.g. on a plasmid or on two compatible plasmids). Thus, the HIV fusion proteins can be obtained from cells which are co-transformed with a repressor plasmid, e.g. the lacI$^q$ repressor plasmid pFDX500. In this way an improved repression of the gene expression during the growth phase can be achieved.

A process is also preferred in which the microorganism contains the recombinant gene according to the present invention, a repressor gene and, in addition, the *E. coli* dnaY-gene (tRNA$^{Arg}$). For this one can for example use cells which are co-transformed with the dnay-lacI$^q$ plasmid pUBS500 instead of pFDX500. The presence of the dnaY gene in a transformed microorganism can lead to a further increase in expression of fusion proteins according to the present invention.

In addition the invention provides a reagent for the determination of anti-HIV antibodies.

This reagent contains:

(a) one or more fusion proteins according to the present invention with at least one antigenic or/and immunogenic determinant of HIV1 or/and HIV2 which are either bound to a solid phase or are so modified that they easily bind to a suitable special solid phase during an incubation step, (b) an incubation buffer which allows the physiological binding of anti-HIV antibodies to the antigenic determinants of the fusion proteins and which at the same time suppresses non-specific binding, (c) a test reagent for the recognition of antigen-bound antibodies and (d) a system for the quantification of the bound specific antibodies.

The antigen can e.g. be present as an antigen-hapten conjugate while molecules are immobilized on the solid phase which react with the hapten. Antigens according to the present invention are preferably conjugated with biotin and therefore bind with a high affinity to a reaction vessel coated with streptavidin. It is, however, also possible to directly bind the antigens absorptively to a solid matrix according to other generally known processes (compare Example 6). All buffers which are usually used for immunochemical reactions are suitable as the incubation buffers. PBS (0.15 mol/l Na phosphate, 0.9% NaCl, pH 7.2) with 10% calf serum and 0.05% Tween 20 is preferably used.

Conjugates of an enzyme (e.g. peroxidase) and polyclonal antibodies against the Fcγ part of human IgG or also enzyme-conjugated HIV antigens are suitable as a test reagent for the recognition of the antigen-bound antibodies.

The bound specific anti-HIV antibodies can be quantitatively determined by addition of a substrate which is cleaved by the enzyme conjugated with the anti-Fcγ antibody or with HIV antigen and whose reaction can be measured. If peroxidase is used as the enzyme then e.g. ABTS® (2,2'-azino-di-[3-ethyl-benzthiazolinesulfonic acid (6)]-diammonium salt) is suitable as the substrate.

Figure 2:
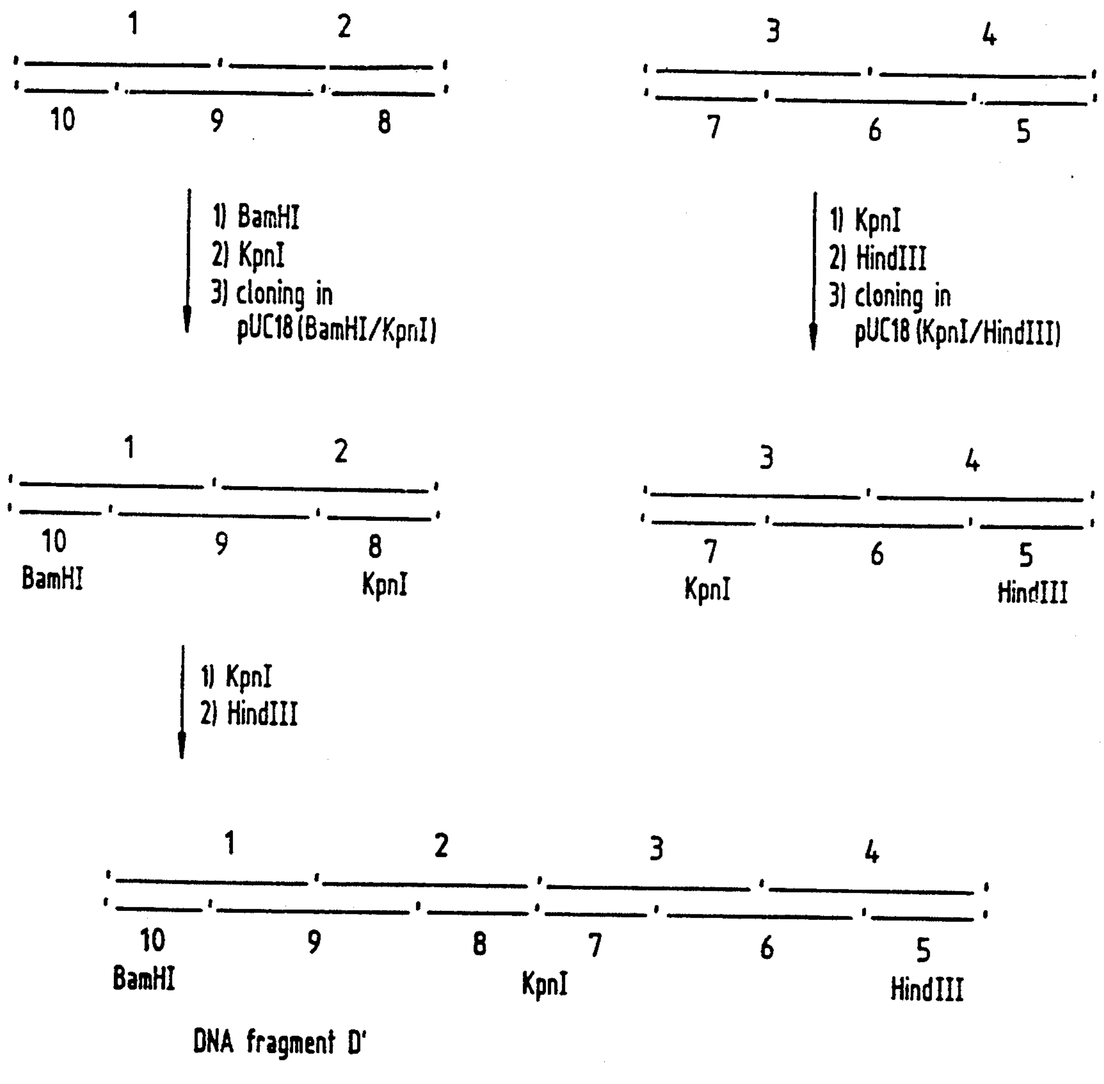

The following examples should elucidate the invention in conjunction with the sequence protocols 1-26 and the FIGS. 1 and 2 in which AA denotes amino acid and B denotes base. They show:

SEQ ID NO:1 shows the amino acid sequence (I) and SEQ ID NO:9 shows the DNA sequence (A) of a HIV fusion protein with a determinant (AA 8 to AA 324, B 20 to B 972) from the gag region of HIV1 (HIV1gag-p17-p24-p15);

SEQ ID NO:2 shows the amino acid sequence (II) and SEQ ID NO:10 shows the DNA sequence (B) of a HIV fusion protein with a determinant (AA 8–241, B 21–725) from the pol region of HIV1 (HIV1pol-p32);

SEQ ID NO:3 shows the amino acid sequence (III) and SEQ ID NO:11 shows the DNA sequence (C) of a HIV fusion protein with a determinant (AA 27–127, B 79–383) from the env region of HIV1 (HIV1env-gp41);

SEQ ID NO:4 shows the amino acid sequence (IV) and SEQ ID NO:12 shows the DNA sequence (D) of a HIV fusion protein with a determinant (AA 7–121, B 19–363) from the env region of HIV2 (HIV2env-gp32);

SEQ ID NO:5 shows the amino acid sequence (V) and SEQ ID NO:13 shows the DNA sequence (E) of a HIV fusion protein with determinants (AA 27–445, B 79–1335) from the env and gag region of HIV1 (HIV1(env-gp41)-(gag-p17-p24-p15));

SEQ ID NO:6 shows the amino acid sequence (VI) and SEQ ID NO:14 shows the DNA sequence (F) of a HIV fusion protein with determinants (AA 7–359, B 19–1079) from the env region of HIV2 and the pol region of HIV1 (HIV2(env-gp32)-HIV1(pol-p32));

SEQ ID NO:7 shows the amino acid sequence (VII) and SEQ ID NO:15 shows the DNA sequence (G) of a HIV fusion protein with determinants (AA 7–786, B 19–2358) from the env region of HIV2, the pol, env and gag region of HIV1 (HIV2(env-gp32)-HIV1(pol -p32)-(enV-gp41)-(gag-p17-p24-p15));

SEQ ID NO:8 shows the amino acid sequence (VIII) and SEQ ID NO:16 shows the DNA sequence (H) of a HIV fusion protein with determinants (AA 7-756, B 19-2268) from the env region of HIV2, the pol, env and gag region of HIV1 and a C-terminal poly(Lys,Arg) sequence (AA 758 - end, B 2272 end) (HIV2(env-gp32)-HIV1(pol-p32)-(env-gp41)-(gag-p17-p24-p15)-poly(Lys,Arg));

FIG. 1 shows the localization of the HIV determinants on the HIV1 genome;

SEQ ID NO:17-26 show the nucleotide sequences of the deoxyoligonucleotides used for the production of the synthetic HIV2(env-gp32) DNA sequence (D');

FIG. 2 shows the cloning strategy for the production of the HIV2(env-gp32) DNA sequence (D').

EXAMPLES

Example 1

1. HIV antigens

Standard methods were used to manipulate DNA as described by Maniatis et al., (1982) in Molecular Cloning: A Laboratory Manual, Cold Spring Harbor Laboratory, Cold Spring Harbor, New York, and by Sherman et al., (1986) in Methods in Yeast Genetics, Cold Spring Harbor Laboratory, Cold Spring Harbor, N.Y.

1.1 Characterization of the HIV1 DNA fragments used

The HIV1 proviral DNA which was used originates from the HIV1-λ-phage clone λWF1.13 from the laboratory of B. H. Hahn (The University of Alabama at Birmingham, Birmingham, U.S.A.). The λWF1.13 clone contains the non-permutated almost complete provirus DNA (ca. 9 kbp long SstI/SstI restriction endonuclease fragment). The proviral DNA was derived from a virus isolate from peripheral blood cells of a patient who died from AIDS. Partial regions from the λWF1.13 DNA (ca. 9 kbp long SstI/SstI fragment, ca. 5.3 kbp long SstI/EcoRI fragment and ca. 3.7 kbp long EcoRI/SstI fragment) were subcloned into the ca. 2.7 kbp long SstI or SstI/EcoRI vector fragment of the *E. coli* vector pUC18 (Yanisch-Perron et al., Gene 33 (1985) 102-119, Vieira and Messing, Gene 19 (1982) 259-268) in the laboratory of Prof. Dr. Dr. H. Wolf (Pettenkofer Institute, Munich). The constructions were denoted: pUC18_WF113_SstI/SstI-9, pUC18_WF113_SstI/EcoRI-19 and pUC18_Wf113_EcoRI/SstI-28. The DNA sequences of the retroviral DNA subfragments of the gag (ca. 960 bp long PvuII/BglII fragment) pol (ca. 710 bp long PvuII/BspMI fragment) and env region (ca. 310 bp long RsaI/HindIII fragment), which were used for the expression of HIV1 fusion proteins, were sequenced according to the dideoxy-chain terminating reaction according to Sanger (Sanger et al., J. Mol. Biol. 143 (1980) 161-178). The localization of these DNA fragments on the HIV genome can be seen in FIG. 1. The fragment A' from the gag region is contained in the DNA sequence A and codes for the HIV1 immunogenic determinants of the fusion protein I. The fragment B' from the pol region is contained in the DNA sequence B and codes for the HIV1 immunogenic determinants of the fusion protein II. The fragment C' from the env region is contained in the DNA sequence C and codes for the HIV1 immunogenic determinants of the fusion protein III.

1.2 Subcloning of the HIV1-gp41 DNA used from the env region of the virus isolate WF1.13 (DNA sequence C')

A ca. 310 bp long RsaI/HindIII fragment of the "envelope" region was isolated from the plasmid pUC18_WF113_EcoRI/SstI-28 and ligated into the 2.7 kbp long pUC18 HincII/HindIII vector fragment (construction: pUC18_WF113_RsaI/HindIII). The subcloned DNA sequence of the RsaI/HindIII fragment of the virus isolate WF1.13 corresponds to the DNA sequence of the virus isolate WMJ-1 from position 1638 to position 1943 (Starcich et al., Cell 45 (1986) 637-648). A ca. 310 long BamHI/HindIII fragment was isolated from the plasmid pUC18_WF113_RsaI/HindIII and subsequently ligated into the 5.2 kbp long vector fragment of pUR288 which had been cleaved with BamHI and HindIII (Rüther and Müller-Hill, EMBO Journal 2 (1983) 1791-1794) (construction: pUR288_WF113_BamHI/HindIII). The DNA junctions which form as a result of the reconstruction were sequenced.

3. Subcloning of the HIV1-p17-p24-p15 DNA used from the gag region of the virus isolate WF1.13 (DNA sequence A')

The plasmid pUC18_WF113_SstI/EcoRI-19 was digested with PvuII, the DNA ends were provided with an EcoRI linker (5'-GGAATTCC-3'), the plasmid DNA was recut with BglII and the protruding 5' ends of the BglII cleavage site were filled up with Klenow polymerase. Afterwards it was recut with EcoRI, the ca. 960 bp long EcoRI/BglII (blunt) fragment was isolated and ligated into the ca. 4.6 kbp long EcoRI/HindIII (blunt) pKK233-2/MYYL vector fragment (see Example 2.4) (construction: pKK233-2/MYYL-p17-p24p15). In order to produce the EcoRI/HindIII (blunt) pKK233-2/MYYL vector fragment the plasmid pKK233-2/MYYL was digested with HindIII, the protruding 5' ends of the HindIII cleavage site were filled up with Klenow polymerase, the plasmid DNA was recleaved with EcoRI and afterwards the vector fragment was isolated.

1.4 Subcloning of the HIV1pol-p32 DNA used from the pol region of the virus isolate WF1.13 (DNA sequence B')

A ca. 970 bp long Asp718I/NdeI fragment from the pol region of HIV1 which contains the ca. 710 bp long PvuII/BspMI fragment used was isolated from the plasmid pUC18_WF113_SstI/EcoRI-19, the protruding 5' ends were filled up with Klenow polymerase and ligated into the HincII cleavage site of the pUC18 vector (Yanisch-Perron et al., (1985) supra) (construction: pUC18_WF113_INT).

The plasmid pUC18_WF113_INT was digested with PvuII, the DNA ends were provided with an EcoRI linker (5'-CGGAATTCCG-3'), the plasmid DNA was digested with BspMI and the protruding 5' ends of the BspMI cleavage site were filled up with Klenow polymerase. Afterwards it was re-cleaved with EcoRI, the ca. 720 bp long EcoRI/BspMI (blunt) fragment was isolated and ligated into the 4.6 kbp long EcoRI/HindIII (blunt) pKK233-2/MYYL vector fragment (construction: pKK233-2/MYYL-pol-p32). In order to produce the EcoRI/HindIII (blunt) pKK233-2/MYYL vector fragment, the plasmid pKK233-2/MYYL (see Example 2.4) was digested with HindIII, the protruding 5' ends of the HindIII cleavage site were removed with SI nuclease, the DNA was recut with EcoRI and afterwards the vector fragment was isolated.

Example 2

HIV2 antigen

2.1 Selection of the antigenic region and gene design

On the basis of the HIV2 DNA sequence published by the working group of L. Montagnier and the protein sequences derived therefrom (Guyader et al., Nature 326 (1987) 662–668), the HIV2 gp32 region of amino acids 48–162 was chosen from the transmembrane region of the HIV2 "envelope" protein gp32 after antigen index analysis (Jameson and Wolf, CABIOS 4 (1988) 181–186; Wolf et al., CABIOS 4 (1988) 187–191). The synthetic HIV2-gp32 partial gene was adapted with respect to codon usage to the codons which are preferably used by the designated host organisms, *E. coli* and yeast, for the expression of the HIV2-gp32 partial protein. The formation of secondary structures was minimized in the gene design and with regard to fusion proteins, suitable singular cleavage sites for restriction endonucleases were also inserted.

2.2 Gene synthesis

The deoxyoligonucleotide used for the production of the synthetic DNA sequence D' and the cloning strategy are shown in detail in SEQ ID NO:17–26 and FIG. 2.

Principle

In each case 5 synthetic deoxyoligonucleotides were joined to form 2 ca. 200 bp long gene blocks each having suitable restiction cleavage sites at their ends, they were purified by gel electrophoresis, cleaved with restriction enzymes and subcloned into the polylinker region of the *E. coli* pUC18 vector. The predetermined DNA sequence of both subcloned gene blocks was confirmed by DNA sequencing. Afterwards both DNA fragments were joined via the single KpnI cleavage site in the pUC18 vector (construction: pUC18 HIV2-gp32).

2.3 Construction of the plasmid pUC18_HIV2-gp32

A) The deoxyoligonucleotides 1, 2, 10, 9 and 8 (see SEQ ID NO:17–26 and FIG. 2) were annealed in a reaction mixture (reaction buffer: 12.5 mol/l Tris/HCl, pH 7.0 and 12.5 mol/l $MgCl_2$), the hybridization product was digested with BamHI and KpnI, the ca. 200 bp long BamHI/KpnI fragment was isolated and subcloned in the pUC18 vector fragment which had been digested with BamHI and KpnI (construction: pUC18_HIV2/BK).

B) The deoxyoligonucleotides 3, 4, 7, 6 and 5 (see SEQ ID NO:17–26 and FIG. 2) were annealed as described under point A), the hybridization product was digested with KpnI and HindIII, the ca. 200 bp long KpnI/HindIII fragment was isolated and subcloned in the pUC18 vector fragment which had been digested with KpnI and HindIII (construction: pUC18_HIV2/KH).

C) The ca. 200 bp long KpnI/HindIII fragment was isolated from the plasmid pUC18_HIV2/KH and ligated into the ca. 2.7 kbp long KpnI/HindIII pUC18_HIV2/BK vector fragment construction: pUC18_HIV2-gp32).

In the construction pUC18_HIV2-gp32, the HIV2-gp32 DNA is under the control of the lac promoter (operator). The HIV2-gp32 DNA forms an open reading frame with the lacZ-α-peptide of the pUC18 polylinker so that during the expression in *E. coli* a lacZ(α-peptide)-HIV2-gp32 fusion protein will be synthesized. The N-terminal lacZ(α-peptide) component is 13 amino acids long.

2.4 Construction of the starting expression plasmid pKK233-2/MYYL

The *E. coli* ATG expression vector pKK233-2 (trc-promoter, NcoI-PstI-HindIII polylinker, rrnB fragment with the 5S-rRNA gene and the transcription terminators T1 and T2) is obtained from the LKB Pharmacia company (Uppsala). The single EcoRI restriction cleavage site in pKK233-2 was destroyed by restriction cleavage with EcoRI, filling up the protruding 5' ends with Klenow polymerase and subsequent "blunt-end" ligation (construction: pKK233-2/E). The NcoI-PstI-HindIII polylinker in the plasmid pKK233-2/E was exchanged for a NcoI-EcoRI-XbaI-HindIII polylinker (construction: pKK233-2/MYYL). This enables the construction of fusion proteins which begin N-terminally with the 4-terminal amino acids of lactose permease (lacY).

In order to produce the plasmid pKK233-2/MYYL the plasmid pKK233-2/E was digested with NcoI and HindIII, the ca. 4.6 kbp long pKK233-2/E NcoI/EcoRI vector fragment was isolated and ligated with the NcoI-EcoRI-XbaI-HindIII polylinker. The NcoI-EcoRI-XbaI-HindIII polylinker was produced by hybridization from the following two deoxyoligonucleotides.

```
                           XbaI
( NcoI)              EcoRI      HindIII
CATGTACTATTTAGAATTCTAGA
    ATGATAAATCTTAAGATCTTCGA
    MetTyrTyrLeu ——>
```

2.5 Construction of the plasmid pKK233-2/MYYL_HIV2-gp32

The ca. 400 bp long EcoRI/HindIII fragment from pUC18_HIV2-gp32 was ligated into the 4.6 kbp long pKK233-2/MYYL EcoRI/HindIII vector fragment. The lacY-HIV2 fusion protein IV is shown in SEQ ID NO:4 and the coding DNA sequence D is shown in SEQ ID NO:12.

2.6 Expression of HIV2-gp32 fusion proteins in *E. coli*

The well-known *E. coli* K12 strains RM82lac+ (met+, lac+ revertants of ED8654; Murray et al., Mol. Gen. Genet. 150 (1977) 53–61), HB101 (Maniatis et al., (1982) supra) and K165 (Neidhardt and Van Bogelen, Biochem. Biophys. Res. Commun. 100 (1981) 884–900) were used as host strains. The expression of HIV2-gp32 fusion proteins was investigated in the absence and presence of the $lacI^q$ repressor plasmid pFDX500 (supra, see page 8). RM82lac+, HB101 and K165 or RM82lac+, HB101 and K165, cotransformed with the $lacI^q$ repressor plasmid pFDX500 were each transformed with the HIV2-gp32 expression plasmids pUC18_HIV2-gp32 and pKK233-2/MYYL_HIV2-gp32 and subsequently cultured at 30° C. in DYT medium (16 g bactotryptone, 10 g yeast extract, 5 g NaCl per liter), supplemented with 50 mg/l ampicillin or 50 mg/l ampicillin plus 50 mg/l kanamycin. After reaching an optical density of 0.6 to 0.8 at 550 nm the cells were induced with IPTG (isopropyl-β-D-thiogalactopyranoside, final concentration 1 mmol/l). 1 ml samples were taken after an induction period of 5 and 20 hours, the cells were centrifuged down, washed with 10 mmol/l phosphate buffer, pH 6.8 and stored at −20° C. before being processed further.

2.7 Cell lysis, SDS polyacrylamide gel electrophoresis (PAGE) and Western blot analysis The cell pellet was re-suspended in 0.25 ml 10 mmol/l phosphate buffer, pH 6.8, and 1 mmol/l EDTA and the cells were lysed by ultrasonic treatment. After centrifugation, 1/5 volume of 5xSDS-sample buffer (1×SDS-sample buffer: 50 mmol/l Tris/HCl, pH 6.8, 1% SDS, 1% mercaptoethanol, 10% glycerol, 0.001% bromophenol blue) was added to the supernatant, the insoluble cell debris fraction was resuspended in 0.3 ml 1×SDS-sample buffer and 6 mol/l urea, the samples were incubated for 5 minutes at 95° C., centrifuged, the proteins were separated by SDS polyacrylamide gel electrophoresis (Laemmli, Nature 227 (1970) 680–685) and subsequently stained with Coomassie Brilliant Blue R. As an alternative or parallel to this the electrophoretically separated proteins were transferred to nitrocellulose filters, fixed (Towbin et al., Proc. Natl. Acad. Sci. 76 (1979) 4350) and the immunoreactivity of HIV fusion proteins to a panel of human HIV1 or HIV1 and HIV2 sera was determined.

A very low expression of HIV2-gp32 of 0.1 to 1% in relation to the total protein of *E. coli* was found in each of the investigated *E. coli* host strains for the construction pUC18_HIV2-gp32. In the presence of the lacI$^q$ repressor plasmid pFDX500 expression values of <0.1% resulted.

For the construction pKK233-2/MYYL_HIV2-gp32 the best expression levels (5–10% in relation to the *E. coli* total protein) in the strain K165 were found in the absence of the lacI$^q$ repressor plasmid. In the presence of the lacI$^q$ repressor plasmid pFDX500 the expression was reduced to 2–5%.

The HIV2-gp32 polypeptides were synthesized in *E. coli* solely as insoluble protein aggregates ("inclusion bodies" "refractile bodies" (RBs); Marston, Biochem. J. 240 (1986) 1–12), which were dissolved out of the insoluble cell debris fraction with 1×SDS-sample buffer or 1×SDS-sample buffer with 6 mol/l urea. The HIV2-gp32 fusion proteins reacted only with human HIV2 sera and showed no cross-reaction with human HIV1 sera in the Western blot analysis.

2.8 Purification of the HIV2-gp32 polypeptide on a larger scale

*E. coli* K165 cells transformed with the plasmid ›KK233-2/MYYL_HIV2-gp32 were grown in a 5 l fermenter at 30° C. in DYT medium with 50 mg/l ampicillin and 1% glucose and the pH was kept constant with a pH-stat (pH 7.5; 1% inoculum of a stationary pre-culture). When the optical density reached 0.8 to 1.0 at 550 nm the cells were induced with 1 mmol/l IPTG (final concentration). After an induction phase of 15 hours the cells were harvested by centrifugation (yield of biomass: 20 g wet weight/l fermentation medium) and washed with 10 mmol/l phosphate buffer, pH 6.8. The cell wall was partially digested with lysozyme and subsequently the cells were lysed mechanically (French press). Afterwards the insoluble HIV2-gp32 RBs were extracted with 6 to 8 mol/l urea from the centrifuged and washed cell debris fraction (see EP-A 0 361475, Example 1) and subsequently purified to a purity of >98% using the usual methods (ion-exchange chromatography and gel filtration in 6 to 8 mmol/l urea, Marston et al., Bio/Technology 2 (1984) 800–804; Cabradilla et al., Biotechnology 4 (1986) 128–133).

Example 3

HIV1-gp41 fusion proteins 3.1 Plasmid: pUC18_WF133_RsaI/HindIII

In the construction pUC18_WF133_RsaI/HindIII (see Example 1) the HIV1-gp41 DNA (RsaI/HindIII fragment) is under the control of the lac promoter. The HIV1-gp41 DNA forms an open reading frame with the lacZ α-peptide DNA of the pUC18 polylinker so that when expressed in *E. coli* a lacZ(α-peptide)-HIV1-gp41 fusion protein should be synthesized which contains 17 N-terminal amino acids and 83 C-terminal amino acids which are not coded by HIV1 DNA. However, the expression of this HIV1-gp41 polypeptide was below the level of detection in the investigated *E. coli* host strains JM109, HB101 and RM82lac+ in the absence and presence of additional lacI$^q$ repressor plasmids (F' episome in JM109 or cotransformation with plasmid pFDX500, see Example 2).

3.2 Construction of the plasmid pKK233-2/MYYL-gp41

The ca. 320 bp long EcoRI/HindIII fragment from the plasmid pUR288_WF113_BamHI/HindIII (see Example 1) was ligated into the ca. 4.6 long pKK233-2/MYYL EcoRI/HindIII vector fragment (construction pKK233-2/MYYL, see Example 2). In this plasmid the HIV1-gp4I DNA is under the control of the trc promoter. The HIV1-gp41 DNA forms an open reading frame with the lacY DNA of the polylinker in the plasmid pKK233-2/MYYL so that when expressed in *E. coli* a HIV1-gp41 fusion protein is formed consisting of the 4 N-terminal amino acids MetTyrTyrLeu of the lactose permease (lacY), 22 amino acids at the fusion site as a result of the construction, 101 amino acids from the envelope gp41 membrane protein and 12 amino acids resulting from the construction at the C-terminus. The DNA sequence C coding for this protein is shown in SEQ ID NO:11 and the protein sequence III derived from this is shown in SEQ ID NO:3.

In *E. coli* HB10I host cells transformed with the plasmid pKK233-2/MYYL-gp41 HIV1-gp4I, fusion protein was only synthesized (expression level: 1 to 2% in relation to the *E. coli* total protein) in the presence of the lacI$^q$ repressor plasmid pFDX500 (co-transformation). The expression analysis (cell growth, induction, SDS PAGE and Western blot analysis) was carried out as described for Example 2.

Surprisingly the expression of the HIV1-gp41 fusion protein could be increased to more than 20% of the *E. coli* total protein if a gene for the arginine-tRNA$^{Arg}$ (anticodons: AGA, AGG) which is rare in *E. coli* is introduced into the host cell. This was achieved by cotransformation with the dnaY-lacI$^q$ plasmid pUBS500 (P 38 38 378.0) instead of the plasmid pFDX500 (supra, see page 8).

Example 4

"Multifunctional HIV fusion proteins

Principle

An artificial HIV fusion gene is produced by means of recombinant DNA technology which is composed of the DNA sub-fragments of several different proviral gene regions and forms an open reading frame. In this way a multifunctional HIV fusion protein is formed which has the desired antigenic regions of different retroviral proteins of a virus (e.g. from the gag, pol and env region of HIV1) and/or the desired antigenic regions of e.g. two different viruses such as HIV1 and HIV2. The development of multifunctional fusion antigens appears very attractive for production reasons (cost savings). In addition, in these fusion antigens the portion of foreign protein sequences which result from the construction is further reduced.

4.1 HIV1(envgp32)-HIV1(polp32) fusion protein

Construction of the expression plasmid pKK233-2/MYYL_gp32_polp32

The plasmid pUC18_WF113_INT (see Example 1) was digested with BamHI and BspMI, the protruding 5' ends of the BamHI and BspMI cleavage sites were filled up with Klenow polymerase, the ca. 730 bp long BamHI (blunt)/BspMI(blunt) fragment was isolated and ligated into the single EcoRV cleavage site of the expression vector pKK233-2/MYYL_HIV2-gp32 (see Example 2). The desired construction pKK233-2/MYYL_gp32_polp32 (correct orientation of the inserted BamHI(blunt)/BspMI(blunt) fragment) was determined by cleavage with the restriction endonucleases EcoRI and XbaI. The DNA coding sequence F is shown in SEQ ID NO:14 and the protein sequence of the HIV2(envpg32)-HIV1(polp32) fusion antigen VI is shown in SEQ ID NO:6.

4.2 HIV1(envgp41)-(gagp17-p24-p15) fusion protein

Construction of the expression plasmid pKK233-2/MYYL_gp41_p24

The plasmid pUC18_WF113_SstI/EcoRI-19 (see Example 1) was digested with BglII, the protruding 5' ends of the BglII cleavage site were filled up with Klenow polymer-se, the plasmid was re-cleaved with PvuII, the ca. ?60 bp long PvuII/BglII(blunt) fragment was isolated and ligated into the single HindIII cleavage site of the HIV1-gp41 expression vector pKK233-2/MYYL-gp41 (see Example 3) after filling up the protruding 5' ends of the HindIII cleavage site. The desired construction, pKK233-2/MYYL_gp41_p24 (correct orientation of the inserted PvuII/BglII(blunt) fragment), was determined with the restriction endonucleases EcoRI and PstI by restriction analysis. The DNA coding sequence E is shown in SEQ ID NO:13 and the protein sequence V of the HIV1envgp41)-(gagp17-p24-p15) fusion protein is shown in SEQ ID NO:5.

4.3

HIV2(envgp31)-HIV1(polp32-envgp41-gagp17-p24-p15 fusion protein

Construction of the expression plasmid pKK233-2/MYYL_gp32_polp32_gp41-p24

The ca. 4.7 kbp long BglII/PvuI vector fragment was isolated from the plasmid pKK233-2/MYYL_gp-32_polp32 (see Example 4.1) and the ca. 2.2 kbp long BamHI/pvuI vector fragment was isolated from the plasmid pKK233-2/MYYL_gp41_p24 (see Example 4.2). Afterwards both the vector fragments were ligated and the desired plasmid construction (pKK233-2/MYYL_gp32_polp32_gp41_p24) was determined by restriction analysis with the restriction endonucleases EcoRI, ApaI and PvuI. The DNA coding sequence G is shown in SEQ ID NO:15 and the protein sequence derived therefrom of the HIV2(envgp32)-HIV1(polp32-envgp41-gagp17-p24-p15) fusion protein VII is shown in SEQ ID NO:7.

In order to express the multifunctional HIV fusion proteins, *E. coli* RM82lac+ cells cotransformed with the dnaY-lacI$^q$ plasmid pUBS500 were used. Up to 20% of the total protein of *E. coli* was synthesized as the fusion proteins; they were insoluble (RBs) and immunologically active. The antigenic determinants of the gag, pol and env region of HIV1 and the env region of HIV2 present in the fusion proteins were all immunologically reactive. The test was carried out using specific monoclonal antibodies (gag) and selected human HIV1 (env, pol) and HIV2 (env) sera. The analyses of expression (cell growth, induction, SDS-PAGE and Western blot analysis) were carried out as described in Example 2.

Example 5

HIV polypeptide with an aid to purification

Construction of the plasmid pKK233-2/MYYL_gp32_polp32_gp41_p2-4_polyArgLys

A polylinker coding for 13 basic amino acids (Lys and Arg) was ligated into the single ApaI cleavage site of the plasmid pKK233-2/MYYL_gp32_polp32_gp-41_p24.

```
(ApaI)                                                      PvuII (ApaI)
      TCTCGTAAAAAGCGTAGACGTAAAAAACGTCGTAAAAAGAAATAGCAGCTGAGGCC
CCGGAGAGCATTTTTCGCATCTGCATTTTTTGCAGCATTTTTCTTTATCGTCGACT
      SerArgLysLysArgArgArgLysLysArgArgLysLysLys***
```

The expression of the HIV2(envgp32)-HIV1(polp-32_envgp41-gagp17-p24-15 poly(Arg Lys) fusion protein in RM82lac+ cells, cotransformed with the dnaY-lacI$^q$ plasmid pUBS500 and the immunological properties of the fusion protein with respect to human HIV1 and HIV2 sera corresponded to those of the HIV2-(envgp32)-HIV1(polp32-envgp41_gagp17-p24-p15) fusion protein (cf. Example 4). The DNA coding sequence H is shown in SEQ ID NO:16 and the protein sequence VIII derived therefrom of the HIV2-(envgp32)-HIV1(polp32-envgp41-gagp17-p24-15 poly-(Arg-Lys) fusion protein is shown in SEQ ID NO:8.

Example 6

Immunological determination of anti-HIV antibodies

In order to coat microtitre plates (Dynatech) the solutions containing antigen in 100 mmol/l sodium carbonate buffer (pH 9.6) are diluted to a concentration of 4 μg/ml and incubated for 18 hours at room temperature.

Subsequently they are re-incubated for one hour at room temperature with bovine serum albumin (10 mg/ml) in phosphate buffered saline (PBS2)).

Before the incubation with human serum or plasma and between the test steps they were washed three times each with 0.5% Tween 20 in demineralized water.

The sample (human serum or plasma) is diluted 100-fold with PBS containing 10% calf serum and incubated for 2 hours at 37° C. in the coated microtitre plate. Subsequently it is washed three times with washing solution (0.5% Tween 20 in demineralized water).

In the second step, it is incubated for one hour at 37° C. with a conjugate of peroxidase and polyclonal antibody against the Fc part of human IgG (POD conjugate) (ca. 30 mU peroxidase/ml in PBS2)) and washed three times with washing solution.

Substrate solution (1.6 mmol/l ABTS®1); 95 mmol/l phosphate-citrate buffer, pH 4.4; 3.1 mmol/l sodium perborate) is added, incubated for one hour at room temperature and the absorbance at 492 nm is determined as a measure for the specific antibodies present in the sample. The results are shown in Table 1

1) 2,2 azino-di-[3-ethylbenzthiazoline-sulfonic acid(6)]-diammonium salt

2) PBS: 0.15 mol/l sodium phosphate; 0.9% NaCl; pH 7.2

TABLE 1

Immunological reactivity of the different HIV antigens (ELISA results [mA(492 nm)]

| Antigen | with anti-HIV pool serum | normal sera (n = 98)* | rel signal |
|---|---|---|---|
| HIVenv-gp41 (Example 3.1) | 1052 | 147 ± 41 | 7.2 |
| HIVenv-gp41 (Example 3.2) | 1308 | 101 ± 16 | 13.0 |
| HIVgag-p17-p24-p15 | 1758 | 61 ± 20 | 29.0 |
| HIVpol-p32 | 902 | 98 ± 17 | 9.0 |
| HIVenv-gp32 | 1706 | 121 ± 31 | 14.0 |

*Number of tested normal human sera

It can be seen from Table 1 that the HIV1 and HIV2 fusion proteins used which have the protein sequences I, II, III and IV (cf. SEQ ID NO: 1, 2, 3 and 4) show no immunological cross-reaction with normal human sera.

Example 7

Western blot determination (according to Methods in Enzymology 92 (1983) 377-391)

For the detection of antigen-specific immune reactions, samples containing antibodies are incubated overnight at room temperature with nitrocellulose strips carrying the antigen in PBS-containing 0.05% Tween 20.

After washing three times they are incubated with POD conjugate (cf. Example 6) (ca. 50 mU/ml). After a further three washing steps with washing solution (Example 6) 4-chloro-1-naphthol is added, incubated for 15 minutes at room temperature and the formation of colour is determined visually.

The immune reaction was classified according to the intensity of the colouration as negative (−), weak (±), distinct (+), intense (++) and very intense (+++). The results are shown in Table II.

Table II shows that fusion proteins according to the present invention react specifically with monoclonal and polyclonal anti-HIV antibodies.

TABLE II

Evaluation of the immunological reactivity in an immunoblot

| | monoclonal antibodies | | polyclonal antibodies | | | | |
|---|---|---|---|---|---|---|---|
| | | | anti-HIV1 | | | anti-HIV2 | |
| Antigen | anti gp41 (env) | anti p24 (gag) | sample 1 | sample 2 | sample 3 | sample 1 | sample 2 |
| HIV1gag-p17 p24-p15 (I) | − | ++ | + | ++ | +/− | + | + |
| HIV1pol-p32 (II) | − | +/− | + | +/− | + | + | +/− |
| HIVenv-gp41 (III) | ++ | − | ++ | + | ++ | − | − |
| HIV2env-gp32 (IV) | − | − | − | − | − | +++ | +++ |
| HIV1(env-gp41)-(gag-p17-p24-p15) (V) | + | ++ | + | ++ | ++ | + | + |
| HIV2(env-gp32)-HIV1(pol-p32) (VI) | − | +/− | + | +/− | + | ++ | ++ |
| HIV2(env-gp32)-HIV1(pol-p32)-(env-gp41)-(gag-p17-p24-p15) (VII) | + | + | +++ | ++ | +++ | ++ | ++ |

− negative,
+/− weak,
+ distinct,
++ intense,
+++ very intense

Example 8

Reagent for the determination of anti-HIV antibodies in human serum or plasma

The reagent contains

Solution 1

0.1 to 1 μg/ml conjugate of antigen and biotin in incubation buffer (PBS) with 10% calf serum.

Solution 2

POD conjugate (conjugate of peroxidase and polyclonal antibodies against the Fcγ part of human IgG, 30 mU POD/ml) in PBS.

Substrate solution (1.6 mmol/l ABTS®; 95 mmol/l phosphate-citrate buffer, pH 4.4; 3.1 mmol/l sodium perborate).

0.01 ml sample is added to a streptavidin-coated polystyrene tube (produced according to EP-A 0 269 092) and incubated for 1 hour at room temperature with 1 ml solution 1. After washing three times with PBS containing 0.05% Tween 20 it is incubated for one hour at room temperature with 1 ml solution 2. After washing three times with PBS containing 0.05% Tween 20 it is incubated for one hour at room temperature with solution 2 and again washed three times. The substrate solution (1.6 mmol/l ABTS ®; 95 mmol/l phosphate citrate buffer, pH 4.4; 3.1 mmol/l sodium perborate) is added, incubated for one hour at room temperature and the absorbance at 492 nm is determined as a measure for the specific antibody present in the sample.

SEQUENCE LISTING ( 1 ) GENERAL INFORMATION:

( i i i ) NUMBER OF SEQUENCES: 26

( 2 ) INFORMATION FOR SEQ ID NO: 1:

( i ) SEQUENCE CHARACTERISTICS:
( A ) LENGTH: 337 amino acid residues
( B ) TYPE: amino acid
( D ) TOPOLOGY: linear ( i i ) MOLECULE TYPE: protein ( x i ) SEQUENCE DESCRIPTION: SEQ ID NO: 1:

Met Tyr Tyr Leu Glu Phe Pro Asp Lys Gly Asn Ser Ser Gln Val Ser
5 10 15

Gln Asn Tyr Pro Ile Val Gln Asn Leu Gln Gly Gln Met Val His Gln
20 25 30

Ala Ile Ser Pro Arg Thr Leu Asn Ala Trp Val Lys Val Ile Glu Glu
35 40 45

Lys Ala Phe Ser Pro Glu Val Ile Pro Met Phe Ser Ala Leu Ser Glu
50 55 60

Gly Ala Thr Pro Gln Asp Leu Asn Thr Met Leu Asn Thr Val Gly Gly
65 70 75 80

His Gln Ala Ala Met Gln Met Leu Lys Glu Thr Ile Asn Glu Glu Ala
85 90 95

Ala Glu Trp Asp Arg Val His Pro Val His Ala Gly Pro Ile Ala Pro
100 105 110

Gly Gln Met Arg Glu Pro Arg Gly Ser Asp Ile Ala Gly Thr Thr Ser
115 120 125

Thr Leu Gln Glu Gln Ile Gly Trp Met Thr Asn Asn Pro Pro Ile Pro
130 135 140

Val Gly Glu Ile Tyr Lys Arg Trp Ile Ile Leu Gly Leu Asn Lys Ile
145 150 155 160

Val Arg Met Tyr Ser Pro Val Ser Ile Leu Asp Ile Arg Gln Gly Pro
165 170 175

Lys Glu Pro Phe Arg Asp Tyr Val Asp Arg Phe Tyr Lys Thr Leu Arg
180 185 190

Ala Glu Gln Ala Ser Gln Glu Val Lys Asn Trp Met Thr Glu Thr Leu
195 200 205

Leu Val Gln Asn Ala Asn Pro Asp Cys Lys Thr Ile Leu Lys Ala Leu
210 215 220

Gly Pro Ala Ala Thr Leu Glu Glu Met Met Thr Ala Cys Gln Gly Val
225 230 235 240

Gly Gly Pro Gly His Lys Ala Arg Val Leu Ala Glu Ala Met Ser Gln
245 250 255

Val Thr Asn Ser Ala Thr Ile Met Met Gln Arg Gly Asn Phe Arg Asn
260 265 270

Gln Lys Lys Thr Val Lys Cys Phe Asn Cys Gly Lys Glu Gly His Ile
275 280 285

Ala Lys Asn Cys Arg Ala Pro Arg Lys Lys Gly Cys Trp Lys Cys Gly
290 295 300

-continued

Lys Glu Gly His Gln Met Lys Asp Cys Thr Glu Arg Gln Ala Asn Phe
305 310 315 320

Leu Gly Lys Ile Ser Leu Ala Val Leu Ala Asp Glu Arg Arg Phe Ser
325 330 335

Ala ( 2 ) INFORMATION FOR SEQ ID NO: 2:

( i ) SEQUENCE CHARACTERISTICS:
( A ) LENGTH: 247 amino acid residues
( B ) TYPE: amino acid
( D ) TOPOLOGY: linear ( i i ) MOLECULE TYPE: protein ( x i ) SEQUENCE DESCRIPTION: SEQ ID NO: 2:

Met Tyr Tyr Leu Glu Phe Arg Cys Asp Lys Cys Gln Leu Lys Gly Glu
5 10 15

Ala Met His Gly Gln Val Asp Cys Ser Pro Gly Ile Trp Gln Leu Asp
20 25 30

Cys Thr His Leu Glu Gly Lys Ile Ile Leu Val Ala Val His Val Ala
35 40 45

Ser Gly Tyr Ile Glu Ala Glu Val Ile Pro Ala Glu Thr Gly Gln Glu
50 55 60

Thr Ala Tyr Phe Ile Leu Lys Leu Ala Gly Arg Trp Pro Val Lys Val
65 70 75 80

Ile His Thr Asp Asn Gly Ser Asn Phe Thr Ser Thr Thr Val Lys Ala
85 90 95

Ala Cys Trp Trp Ala Gly Ile Lys Gln Glu Phe Gly Ile Pro Tyr Asn
100 105 110

Pro Gln Ser Gln Gly Val Val Glu Ser Met Asn Lys Glu Leu Lys Lys
115 120 125

Ile Ile Gly Gln Val Arg Asp Gln Ala Glu His Leu Lys Thr Ala Val
130 135 140

Gln Met Ala Val Phe Ile His Asn Phe Lys Arg Lys Gly Gly Ile Gly
145 150 155 160

Gly Tyr Ser Ala Gly Glu Arg Ile Val Asp Ile Ile Ala Thr Asp Ile
165 170 175

Gln Thr Lys Glu Leu Gln Lys Gln Ile Ile Lys Ile Gln Asn Phe Arg
180 185 190

Val Tyr Tyr Arg Asp Ser Arg Asp Pro Leu Trp Lys Gly Pro Ala Lys
195 200 205

Leu Leu Trp Lys Gly Glu Gly Ala Val Val Ile Gln Asp Asn Ser Glu
210 215 220

Ile Lys Val Val Pro Arg Arg Lys Ala Lys Ile Ile Arg Asp Tyr Gly
225 230 235 240

Lys His Gly Cys Phe Gly Gly
245

( 2 ) INFORMATION FOR SEQ ID NO: 3:

( i ) SEQUENCE CHARACTERISTICS:
( A ) LENGTH: 139 amino acid residues
( B ) TYPE: amino acid
( D ) TOPOLOGY: linear ( i i ) MOLECULE TYPE: protein ( x i ) SEQUENCE DESCRIPTION: SEQ ID NO: 3:

-continued

Met Tyr Tyr Leu Glu Phe Gln Leu Ser Ala Gly Arg Tyr His Tyr Gln
5 10 15

Leu Val Trp Cys Arg Gly Ser Ser Arg Val Gln Thr Arg Gln Leu Leu
20 25 30

Ser Gly Ile Val Gln Gln Gln Asn Asn Leu Leu Arg Ala Ile Glu Thr
35 40 45

Gln Gln His Leu Leu Gln Leu Thr Val Trp Gly Ile Lys Gln Leu Gln
50 55 60

Ala Arg Val Leu Ala Val Glu Arg Tyr Leu Gln Asp Gln Arg Leu Leu
65 70 75 80

Gly Ile Trp Gly Cys Ser Gly Lys Leu Ile Cys Thr Thr Thr Val Pro
85 90 95

Trp Asn Thr Ser Trp Ser Asn Lys Ser Leu Asp Thr Ile Trp His Asn
100 105 110

Met Thr Trp Met Glu Trp Glu Arg Glu Ile Asp Asn Tyr Thr Ser Leu
115 120 125

Ala Val Leu Ala Asp Glu Arg Arg Phe Ser Ala
130 135

( 2 ) INFORMATION FOR SEQ ID NO: 4:

( i ) SEQUENCE CHARACTERISTICS:
( A ) LENGTH: 130 amino acid residues
( B ) TYPE: amino acid
( D ) TOPOLOGY: linear ( i i ) MOLECULE TYPE: protein ( x i ) SEQUENCE DESCRIPTION: SEQ ID NO: 4:

Met Tyr Tyr Leu Glu Phe Gln Gln Gln Gln Gln Leu Leu Asp Val Val
5 10 15

Lys Arg Gln Gln Glu Leu Leu Arg Leu Thr Val Trp Gly Thr Lys Asn
20 25 30

Leu Gln Ala Arg Val Thr Ala Ile Glu Lys Tyr Leu Gln Asp Gln Ala
35 40 45

Arg Leu Asn Ser Trp Gly Cys Ala Phe Arg Gln Val Cys His Thr Thr
50 55 60

Val Pro Trp Val Asn Asp Ser Leu Ala Pro Asp Trp Asp Asn Met Thr
65 70 75 80

Trp Gln Glu Trp Glu Lys Gln Val Arg Tyr Leu Glu Ala Asn Ile Ser
85 90 95

Lys Ser Leu Glu Gln Ala Gln Ile Gln Gln Glu Lys Asn Met Tyr Glu
100 105 110

Leu Gln Lys Leu Asn Ser Trp Asp Ile Arg Ser Lys Leu Gly Cys Phe
115 120 125

Gly Gly
130

( 2 ) INFORMATION FOR SEQ ID NO: 5:

( i ) SEQUENCE CHARACTERISTICS:
( A ) LENGTH: 458 amino acid residues
( B ) TYPE: amino acid
( D ) TOPOLOGY: linear ( i i ) MOLECULE TYPE: protein ( x i ) SEQUENCE DESCRIPTION: SEQ ID NO: 5:

Met Tyr Tyr Leu Glu Phe Gln Leu Ser Ala Gly Arg Tyr His Tyr Gln
5 10 15

Leu Val Trp Cys Arg Gly Ser Ser Arg Val Gln Thr Arg Gln Leu Leu

-continued 20 25 30

Ser Gly Ile Val Gln Gln Gln Asn Asn Leu Leu Arg Ala Ile Glu Thr
35 40 45

Gln Gln His Leu Leu Gln Leu Thr Val Trp Gly Ile Lys Gln Leu Gln
50 55 60

Ala Arg Val Leu Ala Val Glu Arg Tyr Leu Gln Asp Gln Arg Leu Leu
65 70 75 80

Gly Ile Trp Gly Cys Ser Gly Lys Leu Ile Cys Thr Thr Thr Val Pro
85 90 95

Trp Asn Thr Ser Trp Ser Asn Lys Ser Leu Asp Thr Ile Trp His Asn
100 105 110

Met Thr Trp Met Glu Trp Glu Arg Glu Ile Asp Asn Tyr Thr Ser Ser
115 120 125

Asp Lys Gly Asn Ser Ser Gln Val Ser Gln Asn Tyr Pro Ile Val Gln
130 135 140

Asn Leu Gln Gly Gln Met Val His Gln Ala Ile Ser Pro Arg Thr Leu
145 150 155 160

Asn Ala Trp Val Lys Val Ile Glu Glu Lys Ala Phe Ser Pro Glu Val
165 170 175

Ile Pro Met Phe Ser Ala Leu Ser Glu Gly Ala Thr Pro Gln Asp Leu
180 185 190

Asn Thr Met Leu Asn Thr Val Gly Gly His Gln Ala Ala Met Gln Met
195 200 205

Leu Lys Glu Thr Ile Asn Glu Glu Ala Ala Glu Trp Asp Arg Val His
210 215 220

Pro Val His Ala Gly Pro Ile Ala Pro Gly Gln Met Arg Glu Pro Arg
225 230 235 240

Gly Ser Asp Ile Ala Gly Thr Thr Ser Thr Leu Gln Glu Gln Ile Gly
245 250 255

Trp Met Thr Asn Asn Pro Pro Ile Pro Val Gly Glu Ile Tyr Lys Arg
260 265 270

Trp Ile Ile Leu Gly Leu Asn Lys Ile Val Arg Met Tyr Ser Pro Val
275 280 285

Ser Ile Leu Asp Ile Arg Gln Gly Pro Lys Glu Pro Phe Arg Asp Tyr
290 295 300

Val Asp Arg Phe Tyr Lys Thr Leu Arg Ala Glu Gln Ala Ser Gln Glu
305 310 315 320

Val Lys Asn Trp Met Thr Glu Thr Leu Leu Val Gln Asn Ala Asn Pro
325 330 335

Asp Cys Lys Thr Ile Leu Lys Ala Leu Gly Pro Ala Ala Thr Leu Glu
340 345 350

Glu Met Met Thr Ala Cys Gln Gly Val Gly Gly Pro Gly His Lys Ala
355 360 365

Arg Val Leu Ala Glu Ala Met Ser Gln Val Thr Asn Ser Ala Thr Ile
370 375 380

Met Met Gln Arg Gly Asn Phe Arg Asn Gln Lys Lys Thr Val Lys Cys
385 390 395 400

Phe Asn Cys Gly Lys Glu Gly His Ile Ala Lys Asn Cys Arg Ala Pro
405 410 415

Arg Lys Lys Gly Cys Trp Lys Cys Gly Lys Glu Gly His Gln Met Lys
420 425 430

Asp Cys Thr Glu Arg Gln Ala Asn Phe Leu Gly Lys Ile Ser Leu Ala
435 440 445

Val Leu Ala Asp Glu Arg Arg Phe Ser Ala
450 455

-continued ( 2 ) INFORMATION FOR SEQ ID NO: 6:

( i ) SEQUENCE CHARACTERISTICS:
( A ) LENGTH: 376 amino acid residues
( B ) TYPE: amino acid
( D ) TOPOLOGY: linear ( i i ) MOLECULE TYPE: protein ( x i ) SEQUENCE DESCRIPTION: SEQ ID NO: 6:

Met Tyr Tyr Leu Glu Phe Gln Gln Gln Gln Gln Leu Leu Asp Val Val
5 10 15

Lys Arg Gln Gln Glu Leu Leu Arg Leu Thr Val Trp Gly Thr Lys Asn
20 25 30

Leu Gln Ala Arg Val Thr Ala Ile Glu Lys Tyr Leu Gln Asp Gln Ala
35 40 45

Arg Leu Asn Ser Trp Gly Cys Ala Phe Arg Gln Val Cys His Thr Thr
50 55 60

Val Pro Trp Val Asn Asp Ser Leu Ala Pro Asp Trp Asp Asn Met Thr
65 70 75 80

Trp Gln Glu Trp Glu Lys Gln Val Arg Tyr Leu Glu Ala Asn Ile Ser
85 90 95

Lys Ser Leu Glu Gln Ala Gln Ile Gln Gln Glu Lys Asn Met Tyr Glu
100 105 110

Leu Gln Lys Leu Asn Ser Trp Asp Asp Pro Leu Glu Ser Cys Asp Lys
115 120 125

Cys Gln Leu Lys Gly Glu Ala Met His Gly Gln Val Asp Cys Ser Pro
130 135 140

Gly Ile Trp Gln Leu Asp Cys Thr His Leu Glu Gly Lys Ile Ile Leu
145 150 155 160

Val Ala Val His Val Ala Ser Gly Tyr Ile Glu Ala Glu Val Ile Pro
165 170 175

Ala Glu Thr Gly Gln Glu Thr Ala Tyr Phe Ile Leu Lys Leu Ala Gly
180 185 190

Arg Trp Pro Val Lys Val Ile His Thr Asp Asn Gly Ser Asn Phe Thr
195 200 205

Ser Thr Thr Val Lys Ala Ala Cys Trp Trp Ala Gly Ile Lys Gln Glu
210 215 220

Phe Gly Ile Pro Tyr Asn Pro Gln Ser Gln Gly Val Val Glu Ser Met
225 230 235 240

Asn Lys Glu Leu Lys Lys Ile Ile Gly Gln Val Arg Asp Gln Ala Glu
245 250 255

His Leu Lys Thr Ala Val Gln Met Ala Val Phe Ile His Asn Phe Lys
260 265 270

Arg Lys Gly Gly Ile Gly Gly Tyr Ser Ala Gly Glu Arg Ile Val Asp
275 280 285

Ile Ile Ala Thr Asp Ile Gln Thr Lys Glu Leu Gln Lys Gln Ile Ile
290 295 300

Lys Ile Gln Asn Phe Arg Val Tyr Tyr Arg Asp Ser Arg Asp Pro Leu
305 310 315 320

Trp Lys Gly Pro Ala Lys Leu Leu Trp Lys Gly Glu Gly Ala Val Val
325 330 335

Ile Gln Asp Asn Ser Glu Ile Lys Val Val Pro Arg Arg Lys Ala Lys
340 345 350

Ile Ile Arg Asp Tyr Gly Lys Gln Ser Asp Leu Ser Phe Pro Val Leu
355 360 365

-continued

Ala Asp Glu Arg Gly Phe Ser Ala
370 375

( 2 ) INFORMATION FOR SEQ ID NO: 7:

( i ) SEQUENCE CHARACTERISTICS:
( A ) LENGTH: 799 amino acid residues
( B ) TYPE: amino acid
( D ) TOPOLOGY: linear ( i i ) MOLECULE TYPE: protein ( x i ) SEQUENCE DESCRIPTION: SEQ ID NO: 7:

Met Tyr Tyr Leu Glu Phe Gln Gln Gln Gln Gln Leu Leu Asp Val Val
5 10 15

Lys Arg Gln Gln Glu Leu Leu Arg Leu Thr Val Trp Gly Thr Lys Asn
20 25 30

Leu Gln Ala Arg Val Thr Ala Ile Glu Lys Tyr Leu Gln Asp Gln Ala
35 40 45

Arg Leu Asn Ser Trp Gly Cys Ala Phe Arg Gln Val Cys His Thr Thr
50 55 60

Val Pro Trp Val Asn Asp Ser Leu Ala Pro Asp Trp Asp Asn Met Thr
65 70 75 80

Trp Gln Glu Trp Glu Lys Gln Val Arg Tyr Leu Glu Ala Asn Ile Ser
85 90 95

Lys Ser Leu Glu Gln Ala Gln Ile Gln Gln Glu Lys Asn Met Tyr Glu
100 105 110

Leu Gln Lys Leu Asn Ser Trp Asp Asp Pro Leu Glu Ser Cys Asp Lys
115 120 125

Cys Gln Leu Lys Gly Glu Ala Met His Gly Gln Val Asp Cys Ser Pro
130 135 140

Gly Ile Trp Gln Leu Asp Cys Thr His Leu Glu Gly Lys Ile Ile Leu
145 150 155 160

Val Ala Val His Val Ala Ser Gly Tyr Ile Glu Ala Glu Val Ile Pro
165 170 175

Ala Glu Thr Gly Gln Glu Thr Ala Tyr Phe Ile Leu Lys Leu Ala Gly
180 185 190

Arg Trp Pro Val Lys Val Ile His Thr Asp Asn Gly Ser Asn Phe Thr
195 200 205

Ser Thr Thr Val Lys Ala Ala Cys Trp Trp Ala Gly Ile Lys Gln Glu
210 215 220

Phe Gly Ile Pro Tyr Asn Pro Gln Ser Gln Gly Val Val Glu Ser Met
225 230 235 240

Asn Lys Glu Leu Lys Lys Ile Ile Gly Gln Val Arg Asp Gln Ala Glu
245 250 255

His Leu Lys Thr Ala Val Gln Met Ala Val Phe Ile His Asn Phe Lys
260 265 270

Arg Lys Gly Gly Ile Gly Gly Tyr Ser Ala Gly Glu Arg Ile Val Asp
275 280 285

Ile Ile Ala Thr Asp Ile Gln Thr Lys Glu Leu Gln Lys Gln Ile Ile
290 295 300

Lys Ile Gln Asn Phe Arg Val Tyr Tyr Arg Asp Ser Arg Asp Pro Leu
305 310 315 320

Trp Lys Gly Pro Ala Lys Leu Leu Trp Lys Gly Glu Gly Ala Val Val
325 330 335

Ile Gln Asp Asn Ser Glu Ile Lys Val Val Pro Arg Arg Lys Ala Lys
340 345 350

Ile Ile Arg Asp Tyr Gly Lys Gln Ser Asp Arg Ser Ser Arg Val Gln

-continued 355 360 365

Thr Arg Gln Leu Leu Ser Gly Ile Val Gln Gln Gln Asn Asn Leu Leu
370 375 380

Arg Ala Ile Glu Thr Gln Gln His Leu Leu Gln Leu Thr Val Trp Gly
385 390 395 400

Ile Lys Gln Leu Gln Ala Arg Val Leu Ala Val Glu Arg Tyr Leu Gln
405 410 415

Asp Gln Arg Leu Leu Gly Ile Trp Gly Cys Ser Gly Lys Leu Ile Cys
420 425 430

Thr Thr Thr Val Pro Trp Asn Thr Ser Trp Ser Asn Lys Ser Leu Asp
435 440 445

Thr Ile Trp His Asn Met Thr Trp Met Glu Trp Glu Arg Glu Ile Asp
450 455 460

Asn Tyr Thr Ser Ser Asp Lys Gly Asn Ser Ser Gln Val Ser Gln Asn
465 470 475 480

Tyr Pro Ile Val Gln Asn Leu Gln Gly Gln Met Val His Gln Ala Ile
485 490 495

Ser Pro Arg Thr Leu Asn Ala Trp Val Lys Val Ile Glu Glu Lys Ala
500 505 510

Phe Ser Pro Glu Val Ile Pro Met Phe Ser Ala Leu Ser Glu Gly Ala
515 520 525

Thr Pro Gln Asp Leu Asn Thr Met Leu Asn Thr Val Gly Gly His Gln
530 535 540

Ala Ala Met Gln Met Leu Lys Glu Thr Ile Asn Glu Glu Ala Ala Glu
545 550 555 560

Trp Asp Arg Val His Pro Val His Ala Gly Pro Ile Ala Pro Gly Gln
565 570 575

Met Arg Glu Pro Arg Gly Ser Asp Ile Ala Gly Thr Thr Ser Thr Leu
580 585 590

Gln Glu Gln Ile Gly Trp Met Thr Asn Asn Pro Pro Ile Pro Val Gly
595 600 605

Glu Ile Tyr Lys Arg Trp Ile Ile Leu Gly Leu Asn Lys Ile Val Arg
610 615 620

Met Tyr Ser Pro Val Ser Ile Leu Asp Ile Arg Gln Gly Pro Lys Glu
625 630 635 640

Pro Phe Arg Asp Tyr Val Asp Arg Phe Tyr Lys Thr Leu Arg Ala Glu
645 650 655

Gln Ala Ser Gln Glu Val Lys Asn Trp Met Thr Glu Thr Leu Leu Val
660 665 670

Gln Asn Ala Asn Pro Asp Cys Lys Thr Ile Leu Lys Ala Leu Gly Pro
675 680 685

Ala Ala Thr Leu Glu Glu Met Met Thr Ala Cys Gln Gly Val Gly Gly
690 695 700

Pro Gly His Lys Ala Arg Val Leu Ala Glu Ala Met Ser Gln Val Thr
705 710 715 720

Asn Ser Ala Thr Ile Met Met Gln Arg Gly Asn Phe Arg Asn Gln Lys
725 730 735

Lys Thr Val Lys Cys Phe Asn Cys Gly Lys Glu Gly His Ile Ala Lys
740 745 750

Asn Cys Arg Ala Pro Arg Lys Lys Gly Cys Trp Lys Cys Gly Lys Glu
755 760 765

Gly His Gln Met Lys Asp Cys Thr Glu Arg Gln Ala Asn Phe Leu Gly
770 775 780

Lys Ile Ser Leu Ala Val Leu Ala Asp Glu Arg Arg Phe Ser Ala
785 790 795

( 2 ) INFORMATION FOR SEQ ID NO: 8:

( i ) SEQUENCE CHARACTERISTICS:

( A ) LENGTH: 770 amino acid residues
( B ) TYPE: amino acid
( D ) TOPOLOGY: linear ( i i ) MOLECULE TYPE: protein ( x i ) SEQUENCE DESCRIPTION: SEQ ID NO: 8:

Met Tyr Tyr Leu Glu Phe Gln Gln Gln Gln Gln Leu Leu Asp Val Val
5 10 15

Lys Arg Gln Gln Glu Leu Leu Arg Leu Thr Val Trp Gly Thr Lys Asn
20 25 30

Leu Gln Ala Arg Val Thr Ala Ile Glu Lys Tyr Leu Gln Asp Gln Ala
35 40 45

Arg Leu Asn Ser Trp Gly Cys Ala Phe Arg Gln Val Cys His Thr Thr
50 55 60

Val Pro Trp Val Asn Asp Ser Leu Ala Pro Asp Trp Asp Asn Met Thr
65 70 75 80

Trp Gln Glu Trp Glu Lys Gln Val Arg Tyr Leu Glu Ala Asn Ile Ser
85 90 95

Lys Ser Leu Glu Gln Ala Gln Ile Gln Gln Glu Lys Asn Met Tyr Glu
100 105 110

Leu Gln Lys Leu Asn Ser Trp Asp Asp Pro Leu Glu Ser Cys Asp Lys
115 120 125

Cys Gln Leu Lys Gly Glu Ala Met His Gly Gln Val Asp Cys Ser Pro
130 135 140

Gly Ile Trp Gln Leu Asp Cys Thr His Leu Glu Gly Lys Ile Ile Leu
145 150 155 160

Val Ala Val His Val Ala Ser Gly Tyr Ile Glu Ala Glu Val Ile Pro
165 170 175

Ala Glu Thr Gly Gln Glu Thr Ala Tyr Phe Ile Leu Lys Leu Ala Gly
180 185 190

Arg Trp Pro Val Lys Val Ile His Thr Asp Asn Gly Ser Asn Phe Thr
195 200 205

Ser Thr Thr Val Lys Ala Ala Cys Trp Trp Ala Gly Ile Lys Gln Glu
210 215 220

Phe Gly Ile Pro Tyr Asn Pro Gln Ser Gln Gly Val Val Glu Ser Met
225 230 235 240

Asn Lys Glu Leu Lys Lys Ile Ile Gly Gln Val Arg Asp Gln Ala Glu
245 250 255

His Leu Lys Thr Ala Val Gln Met Ala Val Phe Ile His Asn Phe Lys
260 265 270

Arg Lys Gly Gly Ile Gly Gly Tyr Ser Ala Gly Glu Arg Ile Val Asp
275 280 285

Ile Ile Ala Thr Asp Ile Gln Thr Lys Glu Leu Gln Lys Gln Ile Ile
290 295 300

Lys Ile Gln Asn Phe Arg Val Tyr Tyr Arg Asp Ser Arg Asp Pro Leu
305 310 315 320

Trp Lys Gly Pro Ala Lys Leu Leu Trp Lys Gly Glu Gly Ala Val Val
325 330 335

Ile Gln Asp Asn Ser Glu Ile Lys Val Val Pro Arg Arg Lys Ala Lys
340 345 350

Ile Ile Arg Asp Tyr Gly Lys Gln Ser Asp Arg Ser Ser Arg Val Gln
355 360 365

-continued

Thr Arg Gln Leu Leu Ser Gly Ile Val Gln Gln Gln Asn Asn Leu Leu
370 375 380

Arg Ala Ile Glu Thr Gln Gln His Leu Leu Gln Leu Thr Val Trp Gly
385 390 395 400

Ile Lys Gln Leu Gln Ala Arg Val Leu Ala Val Glu Arg Tyr Leu Gln
405 410 415

Asp Gln Arg Leu Leu Gly Ile Trp Gly Cys Ser Gly Lys Leu Ile Cys
420 425 430

Thr Thr Thr Val Pro Trp Asn Thr Ser Trp Ser Asn Lys Ser Leu Asp
435 440 445

Thr Ile Trp His Asn Met Thr Trp Met Glu Trp Glu Arg Glu Ile Asp
450 455 460

Asn Tyr Thr Ser Ser Asp Lys Gly Asn Ser Ser Gln Val Ser Gln Asn
465 470 475 480

Tyr Pro Ile Val Gln Asn Leu Gln Gly Gln Met Val His Gln Ala Ile
485 490 495

Ser Pro Arg Thr Leu Asn Ala Trp Val Lys Val Ile Glu Glu Lys Ala
500 505 510

Phe Ser Pro Glu Val Ile Pro Met Phe Ser Ala Leu Ser Glu Gly Ala
515 520 525

Thr Pro Gln Asp Leu Asn Thr Met Leu Asn Thr Val Gly Gly His Gln
530 535 540

Ala Ala Met Gln Met Leu Lys Glu Thr Ile Asn Glu Glu Ala Ala Glu
545 550 555 560

Trp Asp Arg Val His Pro Val His Ala Gly Pro Ile Ala Pro Gly Gln
565 570 575

Met Arg Glu Pro Arg Gly Ser Asp Ile Ala Gly Thr Thr Ser Thr Leu
580 585 590

Gln Glu Gln Ile Gly Trp Met Thr Asn Asn Pro Pro Ile Pro Val Gly
595 600 605

Glu Ile Tyr Lys Arg Trp Ile Ile Leu Gly Leu Asn Lys Ile Val Arg
610 615 620

Met Tyr Ser Pro Val Ser Ile Leu Asp Ile Arg Gln Gly Pro Lys Glu
625 630 635 640

Pro Phe Arg Asp Tyr Val Asp Arg Phe Tyr Lys Thr Leu Arg Ala Glu
645 650 655

Gln Ala Ser Gln Glu Val Lys Asn Trp Met Thr Glu Thr Leu Leu Val
660 665 670

Gln Asn Ala Asn Pro Asp Cys Lys Thr Ile Leu Lys Ala Leu Gly Pro
675 680 685

Ala Ala Thr Leu Glu Glu Met Met Thr Ala Cys Gln Gly Val Gly Gly
690 695 700

Pro Gly His Lys Ala Arg Val Leu Ala Glu Ala Met Ser Gln Val Thr
705 710 715 720

Asn Ser Ala Thr Ile Met Met Gln Arg Gly Asn Phe Arg Asn Gln Lys
725 730 735

Lys Thr Val Lys Cys Phe Asn Cys Gly Lys Glu Gly His Ile Ala Lys
740 745 750

Asn Cys Arg Ala Ser Arg Lys Lys Arg Arg Arg Lys Lys Arg Arg Lys
755 760 765

Lys Lys
770

( 2 ) INFORMATION FOR SEQ ID NO: 9:

-continued ( i ) SEQUENCE CHARACTERISTICS:
( A ) LENGTH: 1014 base pairs
( B ) TYPE: nucleic acid
( C ) STRANDEDNESS: single
( D ) TOPOLOGY: linear ( x i ) SEQUENCE DESCRIPTION: SEQ ID NO: 9:

```
ATGTACTATT TAGAATTCCC TGACAAAGGA AACAGCAGCC AGGTCAGTCA AAATTACCCT    60
ATAGTGCAGA ACCTACAGGG GCAAATGGTA CATCAGGCCA TATCACCTAG AACTTTAAAT   120
GCATGGGTAA AAGTAATAGA AGAAAAGGCT TTCAGCCCAG AAGTGATACC CATGTTTTCA   180
GCATTATCAG AAGGAGCCAC CCCACAAGAT TTAAATACCA TGCTAAACAC AGTGGGGGGA   240
CATCAAGCAG CCATGCAAAT GTTAAAAGAG ACCATCAATG AGGAAGCTGC AGAATGGGAT   300
AGAGTGCATC CAGTGCATGC AGGGCCTATT GCACCAGGCC AGATGAGAGA ACCAAGGGGA   360
AGTGATATAG CAGGAACTAC TAGTACCCTT CAGGAACAAA TAGGATGGAT GACAAACAAT   420
CCACCTATCC CAGTAGGAGA AATCTATAAA AGATGGATAA TCCTGGGATT AAATAAAATA   480
GTAAGAATGT ATAGTCCTGT TAGTATTCTG GACATAAGAC AAGGACCAAA GGAACCCTTT   540
AGAGACTATG TAGATCGGTT CTATAAAACT TTAAGAGCCG AGCAAGCTTC ACAGGAGGTA   600
AAAAATTGGA TGACAGAAAC CTTGTTGGTC CAAAATGCGA ACCCAGACTG TAAGACTATT   660
CTAAAAGCAT TAGGACCAGC AGCTACACTA GAAGAAATGA TGACAGCATG TCAGGGAGTG   720
GGGGGACCCG GCCATAAGGC AAGAGTGTTG GCTGAAGCAA TGAGCCAAGT AACAAATTCA   780
GCTACCATAA TGATGCAGAG AGGTAATTTT AGGAACCAAA AAAAAACTGT TAAGTGTTTC   840
AATTGTGGCA AAGAAGGGCA CATAGCCAAA AATTGCAGGG CCCCTAGGAA AAAGGGCTGT   900
TGGAAATGTG GAAAGGAAGG ACATCAAATG AAAGATTGTA CTGAGAGACA GGCTAATTTT   960
TTAGGGAAGA TCAGCTTGGC TGTTTTGGCG GATGAGAGAA GATTTTCAGC CTGA        1014
```

( 2 ) INFORMATION FOR SEQ ID NO: 10:

( i ) SEQUENCE CHARACTERISTICS:
( A ) LENGTH: 744 base pairs
( B ) TYPE: nucleic acid
( C ) STRANDEDNESS: single
( D ) TOPOLOGY: linear ( x i ) SEQUENCE DESCRIPTION: SEQ ID NO: 10:

```
ATGTACTATT TAGAATTCCG CTGTGATAAA TGTCAGCTAA AAGGAGAAGC CATGCATGGA    60
CAAGTAGATT GTAGTCCAGG AATATGGCAA CTAGATTGCA CACATTTAGA AGGAAAAATT   120
ATCCTGGTAG CAGTTCATGT AGCCAGTGGC TATATAGAAG CAGAAGTTAT TCCAGCAGAG   180
ACAGGGCAGG AAACAGCATA CTTTATCTTA AAATTAGCAG GAAGATGGCC AGTAAAAGTA   240
ATACATACAG ACAATGGCAG TAATTTCACC AGTACTACGG TTAAGGCCGC CTGTTGGTGG   300
GCGGGGATCA AGCAGGAATT TGGCATTCCC TACAATCCCC AAAGTCAAGG AGTAGTAGAA   360
TCTATGAATA AAGAATTAAA GAAAATTATA GGACAGGTAA GAGATCAGGC TGAACATCTT   420
AAGACAGCAG TACAAATGGC AGTATTTATC CACAATTTTA AAAGAAAAGG GGGGATTGGG   480
GGGTACAGTG CAGGGGAAAG AATAGTAGAC ATAATAGCAA CAGACATACA AACTAAAGAA   540
TTACAAAAAC AAATTATAAA AATTCAAAAT TTTCGGGTTT ATTACAGGGA CAGCAGAGAT   600
CCACTTTGGA AAGGACCAGC AAAGCTCCTC TGGAAAGGTG AAGGGGCAGT AGTAATACAA   660
GACAATAGTG AAATAAAAGT AGTGCCAAGG AGAAAAGCAA AGATCATTAG GGATTATGGA   720
AAACATGGCT GTTTTGGCGG ATGA                                          744
```

( 2 ) INFORMATION FOR SEQ ID NO: 11:

-continued ( i ) SEQUENCE CHARACTERISTICS:
( A ) LENGTH: 420 base pairs
( B ) TYPE: nucleic acid
( C ) STRANDEDNESS: single
( D ) TOPOLOGY: linear ( x i ) SEQUENCE DESCRIPTION: SEQ ID NO: 11:

```
ATGTACTATT TAGAATTCCA GCTGAGCGCC GGTCGCTACC ATTACCAGTT GGTCTGGTGT    60
CGGGGATCCT CTAGAGTCCA GACCAGACAA TTATTGTCTG GAATAGTGCA ACAGCAGAAC   120
AATTTGCTGA GGGCTATTGA GACGCAACAA CATCTGTTGC AACTCACGGT CTGGGGCATC   180
AAACAGCTCC AGGCAAGAGT CCTGGCTGTG GAAAGATACC TACAGGATCA ACGGCTCCTA   240
GGGATTTGGG GTTGCTCTGG AAAACTCATC TGCACCACTA CTGTGCCTTG GAACACTAGT   300
TGGAGTAATA AATCTCTAGA TACAATTTGG CATAACATGA CCTGGATGGA GTGGGAAAGA   360
GAAATTGACA ATTACACAAG CTTGGCTGTT TTGGCGGATG AGAGAAGATT TTCAGCCTGA   420
```

( 2 ) INFORMATION FOR SEQ ID NO: 12:

( i ) SEQUENCE CHARACTERISTICS:
( A ) LENGTH: 393 base pairs
( B ) TYPE: nucleic acid
( C ) STRANDEDNESS: single
( D ) TOPOLOGY: linear ( x i ) SEQUENCE DESCRIPTION: SEQ ID NO: 12:

```
ATGTACTATT TAGAATTCCA ACAGCAACAG CAGTTGTTGG ACGTTGTTAA ACGTCAACAG    60
GAACTGTTGC GTCTGACCGT TTGGGGAACC AAGAACCTTC AGGCTAGAGT TACCGCTATC   120
GAAAAATACC TTCAAGACCA GGCTCGTTTG AACTCCTGGG GTTGCGCTTT TAGACAGGTT   180
TGTCATACCA CGGTACCGTG GGTTAACGAC TCTCTGGCTC CAGACTGGGA CAACATGACC   240
TGGCAGGAAT GGGAAAAGCA AGTTCGTTAC TTGGAAGCTA ACATCTCCAA ATCTCTGGAA   300
CAGGCTCAAA TCCAGCAAGA AAAAAACATG TACGAACTGC AGAAGTTGAA CTCTTGGGAT   360
ATCAGATCTA AGCTTGGCTG TTTTGGCGGA TGA                                393
```

( 2 ) INFORMATION FOR SEQ ID NO: 13:

( i ) SEQUENCE CHARACTERISTICS:
( A ) LENGTH: 1377 base pairs
( B ) TYPE: nucleic acid
( C ) STRANDEDNESS: single
( D ) TOPOLOGY: linear ( x i ) SEQUENCE DESCRIPTION: SEQ ID NO: 13:

```
ATGTACTATT TAGAATTCCA GCTGAGCGCC GGTCGCTACC ATTACCAGTT GGTCTGGTGT    60
CGGGGATCCT CTAGAGTCCA GACCAGACAA TTATTGTCTG GAATAGTGCA ACAGCAGAAC   120
AATTTGCTGA GGGCTATTGA GACGCAACAA CATCTGTTGC AACTCACGGT CTGGGGCATC   180
AAACAGCTCC AGGCAAGAGT CCTGGCTGTG GAAAGATACC TACAGGATCA ACGGCTCCTA   240
GGGATTTGGG GTTGCTCTGG AAAACTCATC TGCACCACTA CTGTGCCTTG GAACACTAGT   300
TGGAGTAATA AATCTCTAGA TACAATTTGG CATAACATGA CCTGGATGGA GTGGGAAAGA   360
GAAATTGACA ATTACACAAG CTCTGACAAA GGAAACAGCA GCCAGGTCAG TCAAAATTAC   420
CCTATAGTGC AGAACCTACA GGGGCAAATG GTACATCAGG CCATATCACC TAGAACTTTA   480
AATGCATGGG TAAAAGTAAT AGAAGAAAAG GCTTTCAGCC CAGAAGTGAT ACCCATGTTT   540
TCAGCATTAT CAGAAGGAGC CACCCCACAA GATTTAAATA CCATGCTAAA CACAGTGGGG   600
GGACATCAAG CAGCCATGCA AATGTTAAAA GAGACCATCA ATGAGGAAGC TGCAGAATGG   660
GATAGAGTGC ATCCAGTGCA TGCAGGGCCT ATTGCACCAG GCCAGATGAG AGAACCAAGG   720
```

-continued

GGAAGTGATA TAGCAGGAAC TACTAGTACC CTTCAGGAAC AAATAGGATG GATGACAAAC 780

AATCCACCTA TCCCAGTAGG AGAAATCTAT AAAAGATGGA TAATCCTGGG ATTAAATAAA 840

ATAGTAAGAA TGTATAGTCC TGTTAGTATT CTGGACATAA GACAAGGACC AAAGGAACCC 900

TTTAGAGACT ATGTAGATCG GTTCTATAAA ACTTTAAGAG CCGAGCAAGC TTCACAGGAG 960

GTAAAAAATT GGATGACAGA AACCTTGTTG GTCCAAAATG CGAACCCAGA CTGTAAGACT 1020

ATTCTAAAAG CATTAGGACC AGCAGCTACA CTAGAAGAAA TGATGACAGC ATGTCAGGGA 1080

GTGGGGGGAC CCGGCCATAA GGCAAGAGTG TTGGCTGAAG CAATGAGCCA AGTAACAAAT 1140

TCAGCTACCA TAATGATGCA GAGAGGTAAT TTTAGGAACC AAAAAAAAAC TGTTAAGTGT 1200

TTCAATTGTG GCAAAGAAGG GCACATAGCC AAAAATTGCA GGGCCCCTAG GAAAAAGGGC 1260

TGTTGGAAAT GTGGAAAGGA AGGACATCAA ATGAAAGATT GTACTGAGAG ACAGGCTAAT 1320

TTTTTAGGGA AGATCAGCTT GGCTGTTTTG GCGGATGAGA GAAGATTTTC AGCCTGA 1377

( 2 ) INFORMATION FOR SEQ ID NO: 14:

( i ) SEQUENCE CHARACTERISTICS:
( A ) LENGTH: 1131 base pairs
( B ) TYPE: nucleic acid
( C ) STRANDEDNESS: single
( D ) TOPOLOGY: linear ( x i ) SEQUENCE DESCRIPTION: SEQ ID NO: 14:

ATGTACTATT TAGAATTCCA ACAGCAACAG CAGTTGTTGG ACGTTGTTAA ACGTCAACAG 60

GAACTGTTGC GTCTGACCGT TTGGGGAACC AAGAACCTTC AGGCTAGAGT TACCGCTATC 120

GAAAAATACC TTCAAGACCA GGCTCGTTTG AACTCCTGGG GTTGCGCTTT TAGACAGGTT 180

TGTCATACCA CGGTACCGTG GGTTAACGAC TCTCTGGCTC CAGACTGGGA CAACATGACC 240

TGGCAGGAAT GGGAAAAGCA AGTTCGTTAC TTGGAAGCTA ACATCTCCAA ATCTCTGGAA 300

CAGGCTCAAA TCCAGCAAGA AAAAAACATG TACGAACTGC AGAAGTTGAA CTCTTGGGAT 360

GATCCTCTAG AGTCCTGTGA TAAATGTCAG CTAAAAGGAG AAGCCATGCA TGGACAAGTA 420

GATTGTAGTC CAGGAATATG GCAACTAGAT TGCACACATT TAGAAGGAAA AATTATCCTG 480

GTAGCAGTTC ATGTAGCCAG TGGCTATATA GAAGCAGAAG TTATTCCAGC AGAGACAGGG 540

CAGGAAACAG CATACTTTAT CTTAAAATTA GCAGGAAGAT GGCCAGTAAA AGTAATACAT 600

ACAGACAATG GCAGTAATTT CACCAGTACT ACGGTTAAGG CCGCCTGTTG GTGGGCGGGG 660

ATCAAGCAGG AATTTGGCAT TCCCTACAAT CCCCAAAGTC AAGGAGTAGT AGAATCTATG 720

AATAAAGAAT TAAAGAAAAT TATAGGACAG GTAAGAGATC AGGCTGAACA TCTTAAGACA 780

GCAGTACAAA TGGCAGTATT TATCCACAAT TTTAAAAGAA AAGGGGGGAT TGGGGGGTAC 840

AGTGCAGGGG AAAGAATAGT AGACATAATA GCAACAGACA TACAAACTAA AGAATTACAA 900

AAACAAATTA TAAAAATTCA AAATTTTCGG GTTTATTACA GGGACAGCAG AGATCCACTT 960

TGGAAAGGAC CAGCAAAGCT CCTCTGGAAA GGTGAAGGGG CAGTAGTAAT ACAAGACAAT 1020

AGTGAAATAA AAGTAGTGCC AAGGAGAAAA GCAAAGATCA TTAGGGATTA TGGAAAACAA 1080

TCAGATCTAA GCTTCCCTGT TTTGGCGGAT GAGAGAGGAT TTTCAGCCTG A 1131

( 2 ) INFORMATION FOR SEQ ID NO: 15:

( i ) SEQUENCE CHARACTERISTICS:
( A ) LENGTH: 2400 base pairs
( B ) TYPE: nucleic acid
( C ) STRANDEDNESS: single
( D ) TOPOLOGY: linear ( x i ) SEQUENCE DESCRIPTION: SEQ ID NO: 15:

-continued

```
ATGTACTATT TAGAATTCCA ACAGCAACAG CAGTTGTTGG ACGTTGTTAA ACGTCAACAG   60
GAACTGTTGC GTCTGACCGT TTGGGGAACC AAGAACCTTC AGGCTAGAGT TACCGCTATC  120
GAAAAATACC TTCAAGACCA GGCTCGTTTG AACTCCTGGG GTTGCGCTTT TAGACAGGTT  180
TGTCATACCA CGGTACCGTG GGTTAACGAC TCTCTGGCTC CAGACTGGGA CAACATGACC  240
TGGCAGGAAT GGGAAAAGCA AGTTCGTTAC TTGGAAGCTA ACATCTCCAA ATCTCTGGAA  300
CAGGCTCAAA TCCAGCAAGA AAAAAACATG TACGAACTGC AGAAGTTGAA CTCTTGGGAT  360
GATCCTCTAG AGTCCTGTGA TAAATGTCAG CTAAAAGGAG AAGCCATGCA TGGACAAGTA  420
GATTGTAGTC CAGGAATATG GCAACTAGAT TGCACACATT TAGAAGGAAA AATTATCCTG  480
GTAGCAGTTC ATGTAGCCAG TGGCTATATA GAAGCAGAAG TTATTCCAGC AGAGACAGGG  540
CAGGAAACAG CATACTTTAT CTTAAAATTA GCAGGAAGAT GGCCAGTAAA AGTAATACAT  600
ACAGACAATG GCAGTAATTT CACCAGTACT ACGGTTAAGG CCGCCTGTTG GTGGGCGGGG  660
ATCAAGCAGG AATTTGGCAT TCCCTACAAT CCCCAAAGTC AAGGAGTAGT AGAATCTATG  720
AATAAAGAAT TAAAGAAAAT TATAGGACAG GTAAGAGATC AGGCTGAACA TCTTAAGACA  780
GCAGTACAAA TGGCAGTATT TATCCACAAT TTTAAAAGAA AAGGGGGGAT TGGGGGGTAC  840
AGTGCAGGGG AAAGAATAGT AGACATAATA GCAACAGACA TACAAACTAA AGAATTACAA  900
AAACAAATTA TAAAAATTCA AAATTTTCGG GTTTATTACA GGGACAGCAG AGATCCACTT  960
TGGAAAGGAC CAGCAAAGCT CCTCTGGAAA GGTGAAGGGG CAGTAGTAAT ACAAGACAAT 1020
AGTGAAATAA AAGTAGTGCC AAGGAGAAAA GCAAAGATCA TTAGGGATTA TGGAAAACAA 1080
TCAGATCGAT CCTCTAGAGT CCAGACCAGA CAATTATTGT CTGGAATAGT GCAACAGCAG 1140
AACAATTTGC TGAGGGCTAT TGAGACGCAA CAACATCTGT TGCAACTCAC GGTCTGGGGC 1200
ATCAAACAGC TCCAGGCAAG AGTCCTGGCT GTGGAAAGAT ACCTACAGGA TCAACGGCTC 1260
CTAGGGATTT GGGGTTGCTC TGGAAAACTC ATCTGCACCA CTACTGTGCC TTGGAACACT 1320
AGTTGGAGTA ATAAATCTCT AGATACAATT TGGCATAACA TGACCTGGAT GGAGTGGGAA 1380
AGAGAAATTG ACAATTACAC AAGCTCTGAC AAAGGAAACA GCAGCCAGGT CAGTCAAAAT 1440
TACCCTATAG TGCAGAACCT ACAGGGGCAA ATGGTACATC AGGCCATATC ACCTAGAACT 1500
TTAAATGCAT GGGTAAAAGT AATAGAAGAA AAGGCTTTCA GCCCAGAAGT GATACCCATG 1560
TTTTCAGCAT TATCAGAAGG AGCCACCCCA CAAGATTTAA ATACCATGCT AAACACAGTG 1620
GGGGGACATC AAGCAGCCAT GCAAATGTTA AAAGAGACCA TCAATGAGGA AGCTGCAGAA 1680
TGGGATAGAG TGCATCCAGT GCATGCAGGG CCTATTGCAC CAGGCCAGAT GAGAGAACCA 1740
AGGGGAAGTG ATATAGCAGG AACTACTAGT ACCCTTCAGG AACAAATAGG ATGGATGACA 1800
AACAATCCAC CTATCCCAGT AGGAGAAATC TATAAAAGAT GGATAATCCT GGGATTAAAT 1860
AAAATAGTAA GAATGTATAG TCCTGTTAGT ATTCTGGACA TAAGACAAGG ACCAAAGGAA 1920
CCCTTTAGAG ACTATGTAGA TCGGTTCTAT AAAACTTTAA GAGCCGAGCA AGCTTCACAG 1980
GAGGTAAAAA ATTGGATGAC AGAAACCTTG TTGGTCCAAA ATGCGAACCC AGACTGTAAG 2040
ACTATTCTAA AAGCATTAGG ACCAGCAGCT ACACTAGAAG AAATGATGAC AGCATGTCAG 2100
GGAGTGGGGG GACCCGGCCA TAAGGCAAGA GTGTTGGCTG AAGCAATGAG CCAAGTAACA 2160
AATTCAGCTA CCATAATGAT GCAGAGAGGT AATTTTAGGA ACCAAAAAAA AACTGTTAAG 2220
TGTTTCAATT GTGGCAAAGA AGGGCACATA GCCAAAAATT GCAGGGCCCC TAGGAAAAAG 2280
GGCTGTTGGA AATGTGGAAA GGAAGGACAT CAAATGAAAG ATTGTACTGA GAGACAGGCT 2340
AATTTTTTAG GGAAGATCAG CTTGGCTGTT TTGGCGGATG AGAGAAGATT TTCAGCCTGA 2400
```

-continued ( 2 ) INFORMATION FOR SEQ ID NO: 16:

( i ) SEQUENCE CHARACTERISTICS:
( A ) LENGTH: 2313 base pairs
( B ) TYPE: nucleic acid
( C ) STRANDEDNESS: single
( D ) TOPOLOGY: linear ( x i ) SEQUENCE DESCRIPTION: SEQ ID NO: 16:

```
ATGTACTATT TAGAATTCCA ACAGCAACAG CAGTTGTTGG ACGTTGTTAA ACGTCAACAG   60
GAACTGTTGC GTCTGACCGT TTGGGGAACC AAGAACCTTC AGGCTAGAGT TACCGCTATC  120
GAAAAATACC TTCAAGACCA GGCTCGTTTG AACTCCTGGG GTTGCGCTTT TAGACAGGTT  180
TGTCATACCA CGGTACCGTG GGTTAACGAC TCTCTGGCTC CAGACTGGGA CAACATGACC  240
TGGCAGGAAT GGGAAAAGCA AGTTCGTTAC TTGGAAGCTA ACATCTCCAA ATCTCTGGAA  300
CAGGCTCAAA TCCAGCAAGA AAAAAACATG TACGAACTGC AGAAGTTGAA CTCTTGGGAT  360
GATCCTCTAG AGTCCTGTGA TAAATGTCAG CTAAAAGGAG AAGCCATGCA TGGACAAGTA  420
GATTGTAGTC CAGGAATATG GCAACTAGAT TGCACACATT TAGAAGGAAA AATTATCCTG  480
GTAGCAGTTC ATGTAGCCAG TGGCTATATA GAAGCAGAAG TTATTCCAGC AGAGACAGGG  540
CAGGAAACAG CATACTTTAT CTTAAAATTA GCAGGAAGAT GGCCAGTAAA AGTAATACAT  600
ACAGACAATG GCAGTAATTT CACCAGTACT ACGGTTAAGG CCGCCTGTTG GTGGGCGGGG  660
ATCAAGCAGG AATTTGGCAT TCCCTACAAT CCCCAAAGTC AAGGAGTAGT AGAATCTATG  720
AATAAAGAAT TAAAGAAAAT TATAGGACAG GTAAGAGATC AGGCTGAACA TCTTAAGACA  780
GCAGTACAAA TGGCAGTATT TATCCACAAT TTTAAAAGAA AAGGGGGGAT TGGGGGGTAC  840
AGTGCAGGGG AAAGAATAGT AGACATAATA GCAACAGACA TACAAACTAA AGAATTACAA  900
AAACAAATTA TAAAAATTCA AAATTTTCGG GTTTATTACA GGGACAGCAG AGATCCACTT  960
TGGAAAGGAC CAGCAAAGCT CCTCTGGAAA GGTGAAGGGG CAGTAGTAAT ACAAGACAAT 1020
AGTGAAATAA AAGTAGTGCC AAGGAGAAAA GCAAAGATCA TTAGGGATTA TGGAAAACAA 1080
TCAGATCGAT CCTCTAGAGT CCAGACCAGA CAATTATTGT CTGGAATAGT GCAACAGCAG 1140
AACAATTTGC TGAGGGCTAT TGAGACGCAA CAACATCTGT TGCAACTCAC GGTCTGGGGC 1200
ATCAAACAGC TCCAGGCAAG AGTCCTGGCT GTGGAAAGAT ACCTACAGGA TCAACGGCTC 1260
CTAGGGATTT GGGGTTGCTC TGGAAAACTC ATCTGCACCA CTACTGTGCC TTGGAACACT 1320
AGTTGGAGTA ATAAATCTCT AGATACAATT TGGCATAACA TGACCTGGAT GGAGTGGGAA 1380
AGAGAAATTG ACAATTACAC AAGCTCTGAC AAAGGAAACA GCAGCCAGGT CAGTCAAAAT 1440
TACCCTATAG TGCAGAACCT ACAGGGGCAA ATGGTACATC AGGCCATATC ACCTAGAACT 1500
TTAAATGCAT GGGTAAAAGT AATAGAAGAA AAGGCTTTCA GCCCAGAAGT GATACCCATG 1560
TTTTCAGCAT TATCAGAAGG AGCCACCCCA CAAGATTTAA ATACCATGCT AAACACAGTG 1620
GGGGGACATC AAGCAGCCAT G AAATGTTA AAAGAGACCA TCAATGAGGA AGCTGCAGAA 1680
TGGGATAGAG TGCATCCAGT GCATGCAGGG CCTATTGCAC CAGGCCAGAT GAGAGAACCA 1740
AGGGGAAGTG ATATAGCAGG AACTACTAGT ACCCTTCAGG AACAAATAGG ATGGATGACA 1800
AACAATCCAC CTATCCCAGT AGGAGAAATC TATAAAAGAT GGATAATCCT GGGATTAAAT 1860
AAAATAGTAA GAATGTATAG TCCTGTTAGT ATTCTGGACA TAAGACAAGG ACCAAAGGAA 1920
CCCTTTAGAG ACTATGTAGA TCGGTTCTAT AAAACTTTAA GAGCCGAGCA AGCTTCACAG 1980
GAGGTAAAAA ATTGGATGAC AGAAACCTTG TTGGTCCAAA ATGCGAACCC AGACTGTAAG 2040
ACTATTCTAA AAGCATTAGG ACCAGCAGCT ACACTAGAAG AAATGATGAC AGCATGTCAG 2100
GGAGTGGGGG GACCCGGCCA TAAGGCAAGA GTGTTGGCTG AAGCAATGAG CCAAGTAACA 2160
```

-continued

AATTCAGCTA CCATAATGAT GCAGAGAGGT AATTTTAGGA ACCAAAAAAA AACTGTTAAG 2220

TGTTTCAATT GTGGCAAAGA AGGGCACATA GCCAAAAATT GCAGGGCCTC TCGTAAAAAG 2280

CGTAGACGTA AAAAACGTCG TAAAAAGAAA TAG 2313

( 2 ) INFORMATION FOR SEQ ID NO: 17:

( i ) SEQUENCE CHARACTERISTICS:
( A ) LENGTH: 100 base pairs
( B ) TYPE: nucleic acid
( C ) STRANDEDNESS: single
( D ) TOPOLOGY: linear ( x i ) SEQUENCE DESCRIPTION: SEQ ID NO: 17:

CGCGGGATCC AGAATTCCAA CAGCAACAGC AGTTGTTGGA CGTTGTTAAA CGTCAACAGG 60

AACTGTTGCG TCTGACCGTT TGGGGAACCA AGAACCTTCA 100

( 2 ) INFORMATION FOR SEQ ID NO: 18:

( i ) SEQUENCE CHARACTERISTICS:
( A ) LENGTH: 100 base pairs
( B ) TYPE: nucleic acid
( C ) STRANDEDNESS: single
( D ) TOPOLOGY: linear ( x i ) SEQUENCE DESCRIPTION: SEQ ID NO: 18:

GGCTAGAGTT ACCGCTATCG AAAAATACCT TCAAGACCAG GCTCGTTTGA ACTCCTGGGG 60

TTGCGCTTTT AGACAGGTTT GTCATACCAC GGTACCCGCG 100

( 2 ) INFORMATION FOR SEQ ID NO: 19:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( x i ) SEQUENCE DESCRIPTION: SEQ ID NO: 19:

CGCGGGTACC GTGGGTTAAC GACTCTCTGG CTCCAGACTG GGACAACATG ACCTGGCAGG 60

AATGGGAAAA GCAAGTTCGT TACTTGGAAG CTAACA 96

( 2 ) INFORMATION FOR SEQ ID NO: 20:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( x i ) SEQUENCE DESCRIPTION: SEQ ID NO: 20:

TCTCCAAATC TCTGGAACAG GCTCAAATCC AGCAAGAAAA AAACATGTAC GAACTGCAGA 60

AGTTGAACTC TTGGGATATC AGATCTAAGC TTGGGC 97

( 2 ) INFORMATION FOR SEQ ID NO: 21:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO: 21:

GCCCAAGCTT AGATCTGATA TCCCAAGAGT TCAACTTCTG CAGTTCGT 48

( 2 ) INFORMATION FOR SEQ ID NO: 22:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( x i ) SEQUENCE DESCRIPTION: SEQ ID NO: 22:

ACATGTTTTT TTCTTGCTGG ATTTGAGCCT GTTCCAGAGA TTTGGAGATG TTAGCTTCCA 60

AGTAACGAAC TTGCTTTTCC CATTCCTGCC AGGTCA 96

( 2 ) INFORMATION FOR SEQ ID NO: 23:

( i ) SEQUENCE CHARACTERISTICS:
( A ) LENGTH: 48 base pairs
( B ) TYPE: nucleic acids
( C ) STRANDEDNESS: single
( D ) TOPOLOGY: linear ( x i ) SEQUENCE DESCRIPTION: SEQ ID NO: 23:

TGTTGTCCCA GTCTGGAGCC AGAGAGTCGT TAACCCACGG TACCCGCG 48

( 2 ) INFORMATION FOR SEQ ID NO: 24:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( x i ) SEQUENCE DESCRIPTION: SEQ ID NO: 24:

CGCGGGTACC GTGGTATGAC AAACCTGTCT AAAAGCGCAA AAAAGCGCAA CCCCAGGAGT 60

( 2 ) INFORMATION FOR SEQ ID NO: 25:

( i ) SEQUENCE CHARACTERISTICS:
( A ) LENGTH: 100 base pairs
( B ) TYPE: nucleic acid
( C ) STRANDEDNESS: single
( D ) TOPOLOGY: linear ( x i ) SEQUENCE DESCRIPTION: SEQ ID NO: 25:

TCAAACGAGC CTGGTCTTGA AGGTATTTTT CGATAGCGGT AACTCTAGCC TGAAGGTTCT 60

TGGTTCCCCA AACGGTCAGA CGCAACAGTT CCTGTTGACG 100

( 2 ) INFORMATION FOR SEQ ID NO: 26:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO: 26:

TTTAACAACG TCCAACAACT GCTGTTGCTG TTGGAATTC" GGATCCCGCG 50

What is claimed is:

1. A fusion protein, comprising at least one antigenic or immunogenic determinant from a protein coded for by an HIV2 env region and having the amino acid sequence set forth in SEQ ID NO: 4, fused to a polypeptide not having an antigenic or immunogenic determinant, said polypeptide consisting essentially of an N-terminal sequence —NH-2—Met—Tyr—Leu.

2. A fusion protein, comprising at least one antigenic or immunogenic determinant from a protein coded for by an HIV1 pol region and an HIV2 env region and having the amino acid sequence set forth in SEQ ID NO: 6, fused to a polypeptide not having an antigenic or immunogenic determinant, said polypeptide consisting essentially of an N-terminal sequence —NH-2—Met—Tyr—Tyr—Leu.

3. A fusion protein, comprising at least one antigenic or immunogenic determinant from a protein coded for by an HIV2 env region, an HIV1 pol region, an HIV1 env region and an HIV1 gag region and having the amino acid sequence set forth in SEQ ID NO: 7, fused to a polypeptide not having an antigenic or immunogenic determinant, said polypeptide consisting essentially of an N-terminal sequence —$NH_2$—Met—Tyr—Tyr—Leu.

4. A fusion protein, comprising at least one antigenic or immunogenic determinant from a protein coded for by an HIV2 env region, an HIV1 pol region, an HIV1 env region, an HIV1gag region, poly(Lys,Arg)n as a C-terminal amino acid sequence, and the amino acid sequence set forth in SEQ ID NO: 8, fused to a polypeptide not having an antigenic or immunogenic determinant, said polypeptide consisting essentially of an N-terminal sequence —$NH_2$—Met—Tyr—Tyr—Leu.

* * * * *